(12) United States Patent
Hassidov et al.

(10) Patent No.: US 10,265,461 B2
(45) Date of Patent: Apr. 23, 2019

(54) COLON CLEANING SYSTEM WITH AUTOMATIC SELF-PURGING FEATURES

(71) Applicant: Motus GI Medical Technologies Ltd., Tirat HaCarmel (IL)

(72) Inventors: Noam Hassidov, Moshav Bustan HaGalil (IL); Eyal Kochavi, Haifa (IL); Roi Tsukran, Rishon-LeZion (IL); Boris Shtul, Moshav Zerufa (IL); Kobi Luleko, Eshchar (IL); Tzach Arnon, Yodfat (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 188 days.

(21) Appl. No.: 14/915,266

(22) PCT Filed: Aug. 28, 2014

(86) PCT No.: PCT/IL2014/050778
§ 371 (c)(1),
(2) Date: Feb. 29, 2016

(87) PCT Pub. No.: WO2015/029039
PCT Pub. Date: Mar. 5, 2015

(65) Prior Publication Data
US 2016/0206805 A1    Jul. 21, 2016

Related U.S. Application Data

(60) Provisional application No. 61/871,463, filed on Aug. 29, 2013.

(51) Int. Cl.
*A61M 3/02* (2006.01)
*A61M 1/00* (2006.01)
*A61B 1/015* (2006.01)

(52) U.S. Cl.
CPC ........ *A61M 3/0216* (2014.02); *A61M 1/0025* (2014.02); *A61M 1/0031* (2013.01);
(Continued)

(58) Field of Classification Search
CPC ........ A61B 1/015; A61M 2005/16863; A61M 2005/16868; A61M 2005/16872
See application file for complete search history.

(56) References Cited

U.S. PATENT DOCUMENTS 5,096,385 A * 3/1992 Georgi .............. A61M 5/16859
                                                            417/18
5,201,908 A    4/1993 Jones
(Continued)

FOREIGN PATENT DOCUMENTS

CN    101301191    11/2008
CN    102046064    5/2011
(Continued)

OTHER PUBLICATIONS

Applicant-Initiated Interview Summary dated Aug. 4, 2017 From the US Patent and Trademark Office Re. U.S. Appl. No. 14/722,400. (3 Pages).
(Continued)

*Primary Examiner* — Nathan R Price
*Assistant Examiner* — Tasnim Mehjabin Ahmed

(57) ABSTRACT

Systems and methods for cleaning a colon or other portion of an intestine include optional use of sensors to detect conditions of blockage of flow of materials within an evacuation channel used to remove fecal material from the body; and devices and methods for purging such blockages from the evacuation channel.

14 Claims, 19 Drawing Sheets

(52) U.S. Cl.
CPC ........ *A61M 1/0037* (2013.01); *A61M 1/0058* (2013.01); *A61M 3/0258* (2013.01); *A61B 1/015* (2013.01); *A61M 2205/3306* (2013.01); *A61M 2205/3324* (2013.01); *A61M 2205/3334* (2013.01); *A61M 2205/3344* (2013.01); *A61M 2205/3379* (2013.01); *A61M 2210/1064* (2013.01)

(56) References Cited

U.S. PATENT DOCUMENTS

| | | | |
|---|---|---|---|
| 5,279,542 | A | 1/1994 | Wilk |
| 5,554,098 | A | 9/1996 | Yabe et al. |
| 5,630,795 | A | 5/1997 | Kuramoto et al. |
| 5,674,182 | A | 10/1997 | Suzuki et al. |
| 5,679,110 | A | 10/1997 | Hamazaki |
| 5,725,476 | A | 3/1998 | Yasui et al. |
| 5,725,477 | A | 3/1998 | Yasui et al. |
| 5,788,650 | A | 8/1998 | Dotolo |
| 6,309,346 | B1 | 10/2001 | Farhadi |
| 6,409,657 | B1 | 6/2002 | Kawano |
| 6,641,553 | B1 | 11/2003 | Chee et al. |
| D536,449 | S | 2/2007 | Nakajima et al. |
| 2005/0033264 | A1 | 2/2005 | Redinger |
| 2005/0154262 | A1 | 7/2005 | Banik et al. |
| 2005/0256464 | A1 | 11/2005 | Pallas |
| 2006/0025729 | A1 | 2/2006 | Leiboff et al. |
| 2006/0069304 | A1 | 3/2006 | Takemoto et al. |
| 2006/0079861 | A1 | 4/2006 | Matasov |
| 2006/0235458 | A1 | 10/2006 | Belson |
| 2007/0015965 | A1 | 1/2007 | Cox et al. |
| 2007/0234716 | A1 | 10/2007 | Hirooka |
| 2009/0143722 | A1 | 6/2009 | Kim |
| 2009/0198212 | A1 | 8/2009 | Timberlake et al. |
| 2009/0292172 | A1 | 11/2009 | Roskopf et al. |
| 2010/0025644 | A1 | 2/2010 | Jockisch |
| 2010/0063358 | A1 | 3/2010 | Kessler |
| 2010/0185150 | A1* | 7/2010 | Zacharias ........... A61M 1/0031 604/119 |
| 2010/0256447 | A1 | 10/2010 | Dubi et al. |
| 2010/0298773 | A1 | 11/2010 | Nitsan et al. |
| 2011/0034865 | A1 | 2/2011 | Wallace |
| 2011/0092892 | A1 | 4/2011 | Nitsan et al. |
| 2011/0105845 | A1 | 5/2011 | Gordon et al. |
| 2012/0289910 | A1 | 11/2012 | Shtul et al. |
| 2013/0085442 | A1 | 4/2013 | Shtul et al. |
| 2013/0296771 | A1 | 11/2013 | Shtul et al. |
| 2015/0257633 | A1 | 9/2015 | Hassidov et al. |
| 2016/0324412 | A1 | 11/2016 | Hassidov et al. |
| 2017/0173256 | A1 | 6/2017 | Hassidov et al. |
| 2018/0020905 | A1* | 1/2018 | Chouinard ............ A61B 1/125 134/18 |
| 2018/0235448 | A1 | 8/2018 | Hassidov et al. |

FOREIGN PATENT DOCUMENTS

| | | |
|---|---|---|
| CN | 102076271 | 5/2011 |
| DE | 3624428 | 1/1988 |
| EP | 1284128 | 2/2003 |
| EP | 1508294 | 2/2005 |
| EP | 2417896 | 2/2012 |
| JP | 50-81088 | 11/1973 |
| JP | 59-183202 | 12/1984 |
| JP | 05-161711 | 6/1993 |
| JP | 06-066605 | 9/1994 |
| JP | 07-178040 | 7/1995 |
| JP | 11-216104 | 8/1999 |
| JP | 2001-061760 | 3/2001 |
| JP | 2003-265595 | 9/2003 |
| JP | 2004-008822 | 1/2004 |
| JP | 2005-095582 | 4/2005 |
| JP | 2005-137423 | 6/2005 |
| JP | 2006-325816 | 12/2006 |
| JP | 2007-278191 | 10/2007 |
| JP | 2007-536073 | 12/2007 |
| JP | 2008-532727 | 8/2008 |
| JP | 2008-206559 | 9/2008 |
| JP | 2011-518584 | 6/2011 |
| JP | 2011-520567 | 7/2011 |
| JP | 2013-516300 | 5/2013 |
| JP | 2013-532023 | 8/2013 |
| WO | WO 92/17219 | 10/1992 |
| WO | WO 99/60934 | 12/1999 |
| WO | WO 00/54653 | 9/2000 |
| WO | WO 01/12102 | 2/2001 |
| WO | WO 2005/110580 | 11/2005 |
| WO | WO 2005/117685 | 12/2005 |
| WO | WO 2006/039511 | 4/2006 |
| WO | WO 2006/101908 | 9/2006 |
| WO | WO 2008/093288 | 8/2008 |
| WO | WO 2008/155776 | 12/2008 |
| WO | WO 2009/040744 | 4/2009 |
| WO | WO 2009/095915 | 8/2009 |
| WO | WO 2009/125387 | 10/2009 |
| WO | WO 2009/143201 | 11/2009 |
| WO | WO 2010/138521 | 12/2010 |
| WO | WO 2011/083450 | 7/2011 |
| WO | WO 2011/083451 | 7/2011 |
| WO | WO 2011/158232 | 12/2011 |
| WO | WO 2015/029039 | 3/2015 |
| WO | WO 2015/075721 | 5/2015 |
| WO | WO 2015/155776 | 10/2015 |
| WO | WO 2015/193896 | 12/2015 |
| WO | WO 2016/189533 | 12/2016 |

OTHER PUBLICATIONS

Notification of Office Action and Search Report dated Nov. 16, 2017 From the State Intellectual Property Office of the People's Republic of China Re. Application No. 201580037467.6. (9 Pages).
International Preliminary Report on Patentability dated Oct. 20, 2016 From the International Bureau of WIPO Re. Application No. PCT/IL2015/050379. (9 Pages).
Communication Relating to the Results of the Partial International Search dated Feb. 24, 2015 From the International Searching Authority Re. Application No. PCT/IL2014/051014.
International Preliminary Report on Patentability dated Jun. 2, 2016 From the International Bureau of WIPO Re. Application No. PCT/IL2014/051014.
International Preliminary Report on Patentability dated Mar. 10, 2016 From the International Bureau of WIPO Re. Application No. PCT/IL2014/050778.
International Search Report and the Written Opinion dated May 6, 2015 From the International Searching Authority Re. Application No. PCT/IL2014/051014.
International Search Report and the Written Opinion dated Dec. 8, 2014 From the International Searching Authority Re. Application No. PCT/IL2014/050778.
International Search Report and the Written Opinion dated Oct. 13, 2015 From the International Searching Authority Re. Application No. PCT/IL2015/050615.
International Search Report and the Written Opinion dated Feb. 16, 2016 From the International Searching Authority Re. Application No. PCT/IL2015/050379.
International Search Report and the Written Opinion dated Oct. 16, 2015 From the International Searching Authority Re. Application No. PCT/IL2015/050379.
Invitation to Pay Additional Fees dated Aug. 12, 2015 From the International Searching Authority Re. Application No. PCT/IL2015/050379.
Ambrose et al. "Physiological Consequences of Orthograde Lavage Bowel Preparation for Elective Colorectal Surgery: A Review", Journal of the Royal Society of Medicine,76(9): 767-771, Sep. 1983. p.768, 2nd Paragraph.
International Search Report and the Written Opinion dated Sep. 11, 2016 From the International Searching Authority Re. Application No. PCT/IL2016/050544.
Restriction Official Action dated Nov. 16, 2016 From the U.S. Patent and Trademark Office Re. U.S. Appl. No. 14/722,400. (11 pages).

(56) References Cited

OTHER PUBLICATIONS

Communication Pursuant to Article 94(3) EPC dated Jan. 3, 2017 From the European Patent Office Re. Application No. 15735746.8. (4 Pages).
Notice of Reason for Rejection dated Jan. 31, 2017 From the Japan Patent Office Re. Application No. 2016-553662. (3 Pages).
Translation of Notice of Grounds of Rejection dated Jan. 31, 2017 From the Japan Patent Office Re. Application No. 2016-553662. (4 Pages).
Restriction Official Action dated Feb. 28, 2017 From the U.S. Patent and Trademark Office Re. U.S. Appl. No. 14/722,400. (11 pages.
Restriction Official Action dated Mar. 29, 2017 From the U.S. Patent and Trademark Office Re. U.S. Appl. No. 15/108,601. (10 Pages).
Official Action dated May 31, 2017 From the U.S. Patent and Trademark Office Re. U.S. Appl. No. 15/108,601. (46 Pages).
Official Action dated Jun. 6, 2017 from the U.S. Patent and Trademark Office Re. U.S. Appl. No. 14/722,400. (51 pages).
Notice of Reason for Rejection dated Jun. 27, 2017 From the Japan Patent Office Re. Application No. 2016-553662. (3 Pages).
Translation of Notice of Grounds of Rejection dated Jun. 27, 2017 From the Japan Patent Office Re. Application No. 2016-553662. (3 Pages).
International Preliminary Report on Patentability dated Dec. 29, 2016 From the International Bureau of WIPO Re. Application No. PCT/IL2015/050615. (8 Pages).
Translation of Notification of Office Action dated Nov. 16, 2017 From the State Intellectual Property Office of the People's Republic of China Re. Application No. 201580037467.6. (2 Pages).
International Preliminary Report on Patentability dated Dec. 7, 2017 From the International Bureau of WIPO Re. Application No. PCT/IL2016/050544. (8 Pages).
Supplementary European Search Report and the European Search Opinion dated Dec. 1, 2017 From the European Patent Office Re. Application No. 15776016.6. (10 Pages).
Applicant-Initiated Interview Summary dated Sep. 14, 2017 From the U.S. Patent and Trademark Office Re. U.S. Appl. No. 15/108,601. (3 pages).
Official Action dated Oct. 19, 2017 From the U.S. Patent and Trademark Office Re. U.S. Appl. No. 15/108,601. (38 pages).
Official Action dated Nov. 8, 2017 From the U.S. Patent and Trademark Office Re. U.S. Appl. No. 14/722,400. (23 pages).
European Search Report and the European Search Opinion dated Mar. 23, 2018 From the European Patent Office Re. Application No. 17196947.0. (7 Pages).
Official Action dated Apr. 6, 2018 From the U.S. Patent and Trademark Office Re. U.S. Appl. No. 15/301,968. (52 pages).
Translation dated Jul. 24, 2018 of Notice of Reasons for Rejection dated Jul. 10, 2018 From the Japan Patent Office Re. Application No. 2016-537600 and Its Summary in English. (9 Pages).
Restriction Official Action dated Oct. 4, 2018 From the U.S. Patent and Trademark Office Re. U.S. Appl. No. 15/959,397. (10 pages).
Notice of Reasons for Rejection dated Jul. 10, 2018 From the Japan Patent Office Re. Application No. 2016-537600 and Its Summary in English. (9 Pages).
Notice of Grounds of Rejection dated Sep. 5, 2018 From the Japan Patent Office Re. Application No. 2016-528831. (6 Pages).
Translation dated Sep. 20, 2018 of Notice of Grounds of Rejection dated Sep. 5, 2018 From the Japan Patent Office Re. Application No. 2016-528831. (7 Pages).

\* cited by examiner

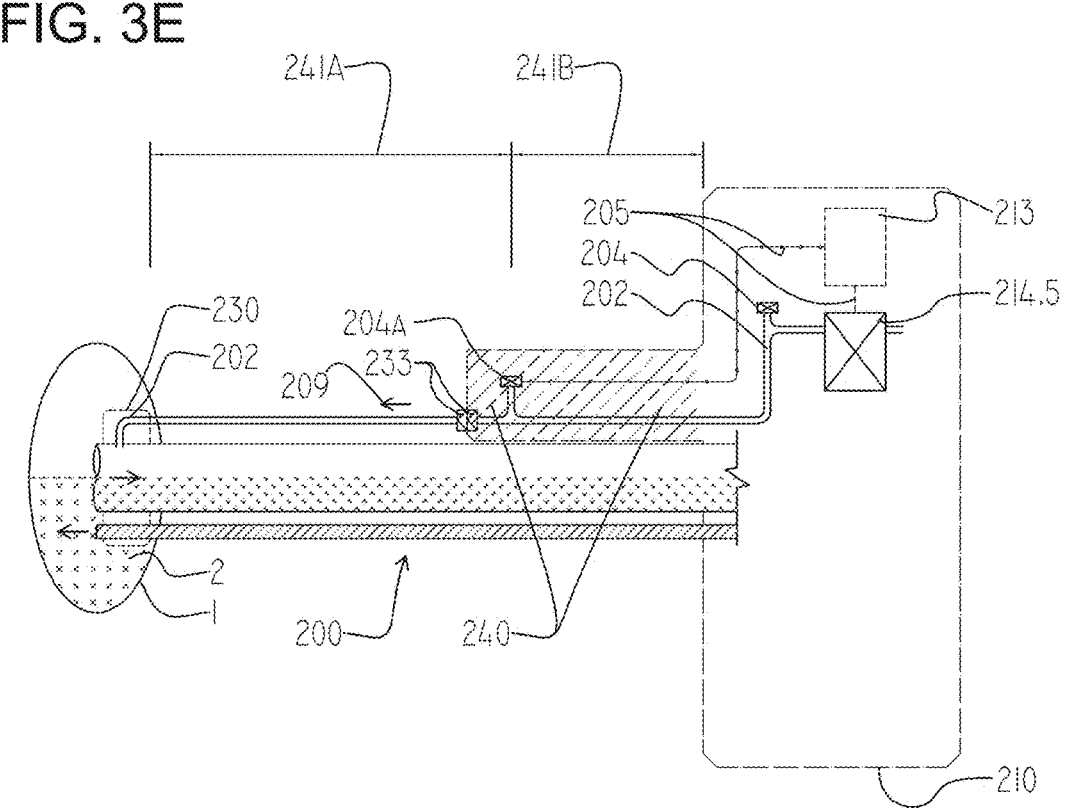

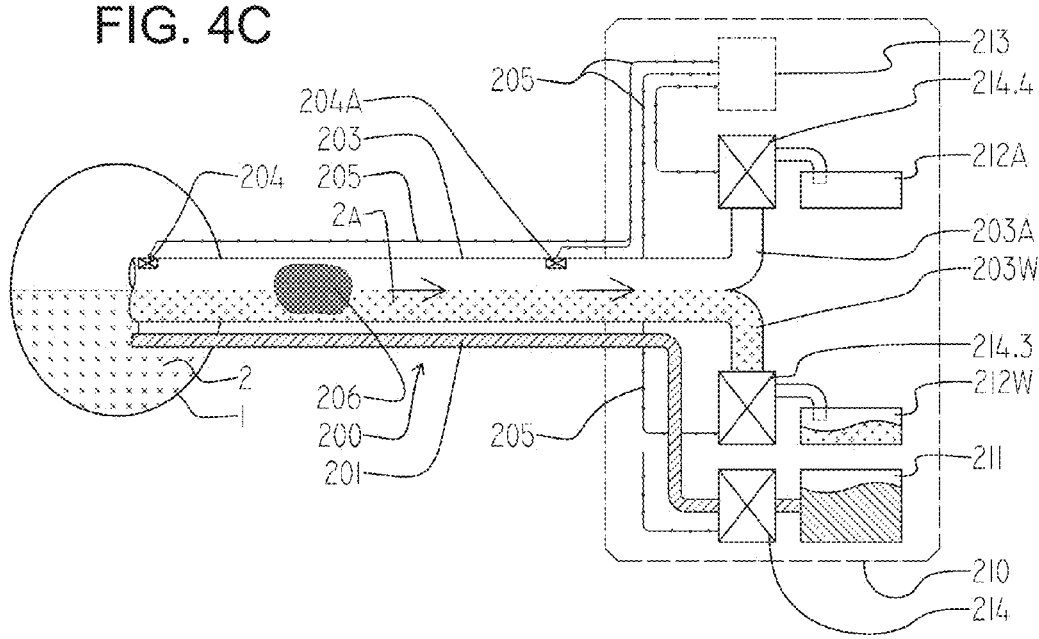
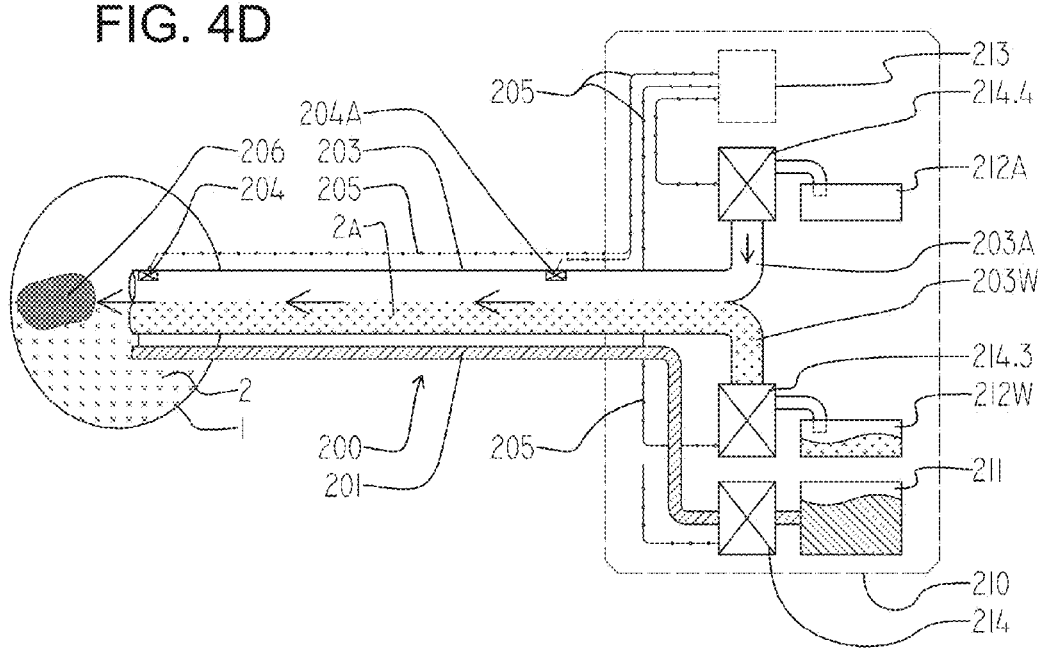

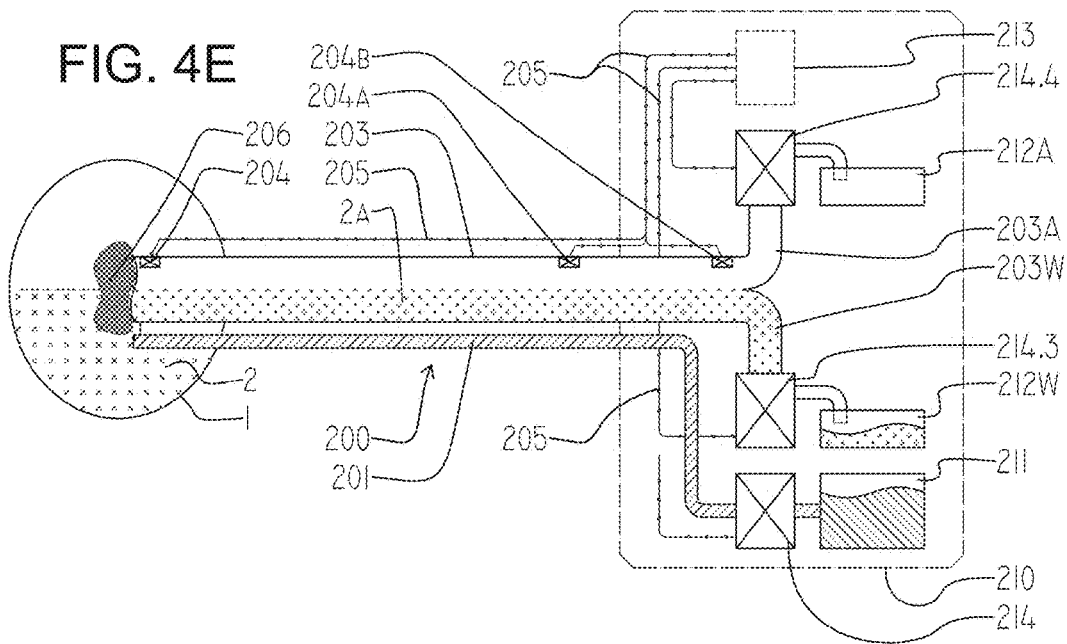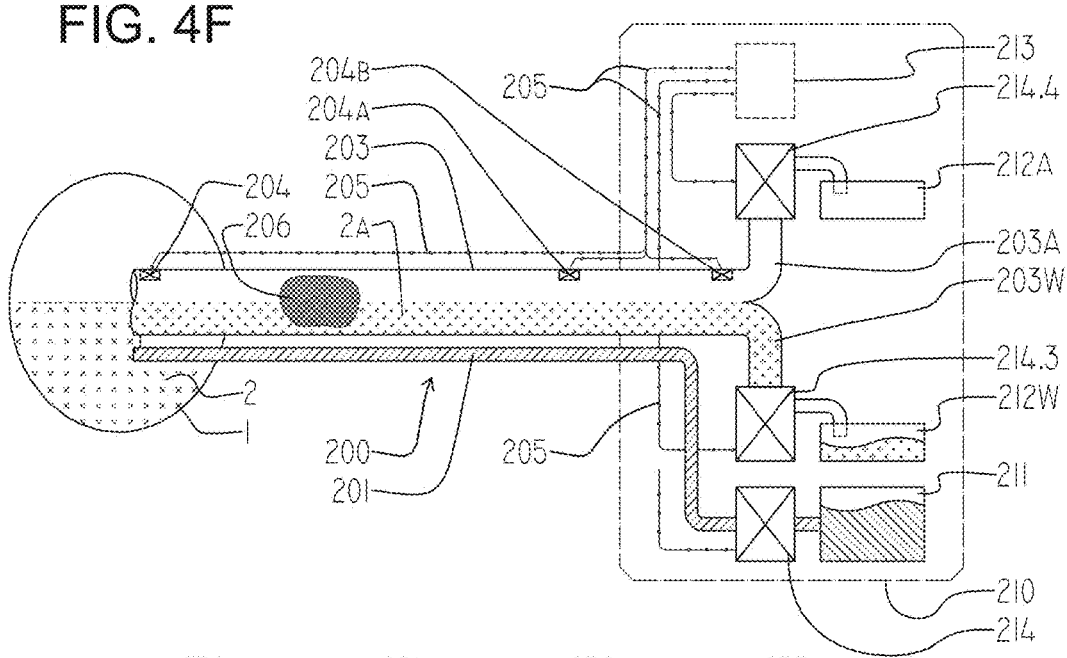

US 10,265,461 B2

COLON CLEANING SYSTEM WITH AUTOMATIC SELF-PURGING FEATURES

RELATED APPLICATIONS

This application is a National Phase of PCT Patent Application No. PCT/IL2014/050778 having International filing date of Aug. 28, 2014, which claims the benefit of priority under 35 USC § 119(e) of U.S. Provisional Patent Application No. 61/871,463 filed on Aug. 29, 2013. The contents of the above applications are all incorporated by reference as if fully set forth herein in their entirety.

FIELD AND BACKGROUND OF THE INVENTION

The present invention, in some embodiments thereof, relates to a system for cleaning a colon or other body lumen, and, more particularly but not exclusively, to systems and methods for cleaning comprising automated self-cleaning features.

Current gastrointestinal technology includes various methods for cleaning fecal matter from a colon. In cases of impacted feces following long constipation, colon cleaning itself can be a goal of a procedure. In other cases, colon cleaning is necessary or desirable to enable unimpeded inspection of the colon tissues and/or to facilitate diagnostic examinations and/or treatment of those tissues.

A colonoscope provides means for optically and/or electronically imaging the colon and its contents. In some methods of colon observation, imaging occurs while flushing or washing a portion of the colon with an irrigating fluid. Irrigating fluid, fecal matter and/or other colon contents are drawn out of the colon by suction and/or other methods for transporting matter out of the body.

In some cases, a working channel of a colonoscope provides irrigation to the colon. In some cases, a working channel of a colonoscope transports fecal materials from the body. In some cases, irrigation and/or suction channels are connectable to the colonoscope for coordinated use of a cleaning system and colonoscope. Cleaning systems with features intended to purge developed blockages which cause problems by preventing evacuation flow are known in the art.

The following patent applications pertain to the field of endeavor of the current application: U.S. Patent Application 2010/0185056 by Tal Gordon et al.; U.S. Patent Application 2011/0105845 by Tal Gordon et al.; and U.S. Patent Application 2012/0101336 by Yoav Hirsch et al.

SUMMARY OF THE INVENTION

According to an aspect of some embodiments of the present invention, there is provided a system for cleaning an intestine, comprising: an evacuation lumen for evacuating irrigation fluid from the intestine; a variable output pressure source; at least one sensor, positioned to detect an environmental condition in or near the evacuation lumen; and a controller configured to: determine a developing blockage of the evacuation lumen based on reporting from the at least one sensor, and vary the pressure from the pressure source for purging of the developing blockage based on the determination.

According to some embodiments of the invention, the pressure source is operable to alternately apply proximally-directed and distally-directed pressure gradients to the evacuation lumen.

According to some embodiments of the invention, the evacuation lumen is at least as long as a human colon.

According to some embodiments of the invention, the developing blockage is determined while the rate of evacuation matches or exceeds the rate of introduction of the irrigation fluid to the intestine.

According to some embodiments of the invention, the developing blockage comprises less than a 50% occlusion of a cross-section of an evacuation lumen.

According to some embodiments of the invention, the developing blockage comprises less than a 10% occlusion of a cross-section of an evacuation lumen.

According to some embodiments of the invention, the developing blockage comprises an onset of a decreasing rate of evacuation due to increasing obstruction of an evacuation lumen.

According to some embodiments of the invention, the developing blockage comprises a blockage detected within 100 msec of reaching an occlusion of more than 50% of an evacuation lumen.

According to some embodiments of the invention, the developing blockage comprises a blockage detected within 50 msec of reaching an occlusion of more than 80% of an evacuation lumen.

According to some embodiments of the invention, the varying of pressure is configured to comprise at least two cycles of increasing and then decreasing the distally directed pressure.

According to some embodiments of the invention, the controller is configured to redetermine blockage during the varying of pressure.

According to some embodiments of the invention, the controller is configured to adjust the varying of pressure based upon the finding of the redetermination being an unchanged blockage.

According to some embodiments of the invention, the adjustment comprises a termination of pressure variation.

According to some embodiments of the invention, the adjustment comprises an increasing of pressure variation.

According to some embodiments of the invention, the determination comprises determination of a location in the system of a developing blockage, the determination of a location being a basis for the variation of pressure.

According to an aspect of some embodiments of the present invention, there is provided the system of claim 1, with at least two of the at least one sensor selected from a group consisting of: a) a sensor positioned on external surface of a distal portion of the evacuation lumen and external to the lumen; b) a sensor positioned within the evacuation lumen and within 5 mm of a distal end of the evacuation lumen; c) a sensor positioned within the evacuation lumen and 5-30 mm of a distal end of the evacuation lumen; d) a sensor positioned within the evacuation lumen and 3-160 cm from a distal end of the evacuation lumen; e) a sensor positioned within the evacuation lumen and 160-250 cm from a distal end of the evacuation lumen; f) a sensor positioned within the evacuation lumen and at least 250 cm from a distal end of the evacuation lumen; and g) a sensor positioned within a fluid supply tube which supplies a fluid flow to a distal portion of the evacuation lumen.

According to some embodiments of the invention, the pressure source comprises a first pump operable to pump material distally through the evacuation lumen.

According to some embodiments of the invention, the first pump is also operable to pump material proximally through the evacuation lumen.

According to some embodiments of the invention, the pressure source comprises a second pump operable to pump material proximally through the evacuation lumen.

According to some embodiments of the invention, the pressure source comprises a valve and vacuum source inlet, the valve being controllable for connecting and disconnecting the evacuation lumen with the vacuum source inlet.

According to some embodiments of the invention, the pressure source comprises a valve and a pressurized fluid inlet, the valve being controllable for connecting and disconnecting the evacuation lumen with the pressurized fluid inlet.

According to some embodiments of the invention, the at least one sensor comprises an optical sensor.

According to some embodiments of the invention, the optical sensor senses at least one of the group consisting of a turbidity, a particle size, a particle number, or a particle spectrum.

According to some embodiments of the invention, the at least one sensor comprises a sensor for sensing a bulk material property.

According to some embodiments of the invention, the bulk material property is at least one of the group consisting of a pH, a conductance, a solute concentration, or an osmotic pressure.

According to some embodiments of the invention, the at least one sensor comprises a flow sensor.

According to some embodiments of the invention, the at least one sensor comprises a fluid pressure sensor.

According to some embodiments of the invention, the determination of a developing blockage comprises at least one of the group consisting of a change in a sensed: a) pressure from one or more sensors; b) pressure difference among two or more sensors; c) flow; d) optical property; and e) bulk material property.

According to some embodiments of the invention, the system comprises a plurality of evacuation lumens.

According to some embodiments of the invention, the pressure applied to each of the plurality of evacuation lumens by the pressure source is individually controllable.

According to some embodiments of the invention, the evacuation pressure in a first of the plurality of evacuation lumens is distally directable, simultaneously with the evacuation pressure in a second of the plurality of evacuation lumens being proximally directed.

According to some embodiments of the invention, the plurality of evacuation lumens comprises a joining connection within 100 cm of the distal end of the lumens, sized for the passage of evacuated material.

According to some embodiments of the invention, the at least one sensor is positioned to detect pressure in the evacuation lumen; and the determination of a developing blockage comprises determination of a pressure change in the evacuation lumen.

According to some embodiments of the invention, the determination of a pressure change comprises determination of an onset of a pressure change.

According to some embodiments of the invention, the determination of a pressure change comprises determination of a change of at least 10 mmHg pressure within 100 msec.

According to some embodiments of the invention, the determination of a pressure change comprises determination of a change of at least 20 mmHg pressure within 150 msec.

According to some embodiments of the invention, the determination of a pressure change comprises determination of a change of at least 30 mmHg pressure within 200 msec.

According to some embodiments of the invention, the determination of a pressure change comprises determination of a differential change between two of the at least one sensor of at least 10 mmHg pressure within 100 msec.

According to an aspect of some embodiments of the present invention, there is provided a method for purging blockage of an evacuation lumen of an intestinal cleaning system, comprising: inserting an evacuation lumen at least 50 cm into a colon; evacuating waste from a colon proximally through the evacuation lumen; automatically detecting a developing blockage of the evacuation lumen; and initiating variation of the pressure in the evacuation lumen based on the automatic detection of a blockage.

According to some embodiments of the invention, the inserting is to within 20 cm of the distal end of the colon.

According to some embodiments of the invention, the method comprises: automatically determining that the developing blockage has been reduced; and stopping the automatic pressure variation.

According to some embodiments of the invention, the pressure variation comprises alternating the pressure in the evacuation lumen between distally-directed and proximally-directed pressures.

According to some embodiments of the invention, the pressure variation is at a frequency above 1 Hz.

According to some embodiments of the invention, the pressure variation reverses the pressure between distally-directed and proximally-directed at a frequency above 1 Hz.

According to some embodiments of the invention, the pressure variation is at a frequency above 5 Hz.

According to some embodiments of the invention, the pressure variation reverses the pressure from distally-directed to proximally-directed at a frequency above 5 Hz.

According to some embodiments of the invention, the automatic detection is performed at least 5 times per minute.

According to some embodiments of the invention, the evacuation lumen comprises a plurality of evacuation sub-lumens arranged alongside each other, and the variation of pressure is controlled so that a distally-directed pressure is applied to one sub-lumen while a proximally-directed pressure is applied to another sub-lumen.

According to some embodiments of the invention, the plurality of sub-lumens are joined by a connection allowing fluid communication, the join being within 20 mm of the distal end of the sub-lumens.

According to some embodiments of the invention, the initiated variation of pressure is modulated based on the determined degree of developing blockage.

According to some embodiments of the invention, the initiated variation of pressure is modulated based on the determined location of developing blockage.

According to some embodiments of the invention, the detecting of a developing blockage comprises a sensed reduction of flow in the evacuation lumen.

According to some embodiments of the invention, the detecting of a developing blockage comprises a sensed pressure change in the evacuation lumen.

According to some embodiments of the invention, the developing blockage detected is associated with a determined blockage location, and variation of pressure is modulated based on the blockage location.

According to some embodiments of the invention, the method comprises changing a pressure of irrigation fluid supplied to the colon at the distal end of the evacuation lumen.

According to some embodiments of the invention, the supplied irrigation fluid washes the distal end of the evacuation lumen.

According to an aspect of some embodiments of the present invention, there is provided a system for cleaning an intestine, comprising: a plurality of evacuation lumens for evacuating irrigation fluid from the intestine; a pressure source operable to individually apply alternately proximally-directed and distally-directed pressure gradients to each of the plurality of evacuation lumens; at least one sensor, positioned to detect an environmental condition in or near the plurality of evacuation lumens; at least one of the at least one sensor being configured to report a level of intracolonic pressure; and a controller configured to: determine the presence of blockage of the evacuation lumen based on reporting from the at least one sensor, determine if the level of intracolonic pressure satisfies a pressure safety condition, and vary the pressure from the pressure source for purging of the blockage based on the blockage presence only if the pressure safety condition is met.

According to some embodiments of the invention, the pressure safety condition is met by an intracolonic pressure of less than 150 mmHg.

According to some embodiments of the invention, the pressure safety condition is met by an intracolonic pressure of less than 200 mmHg.

According to an aspect of some embodiments of the present invention, there is provided a system for cleaning an intestine, comprising: an evacuation lumen for evacuating irrigation fluid from the intestine; a pressure source operable to alternately apply proximally-directed and distally-directed pressure gradients to the evacuation lumen; at least one sensor, positioned to detect an environmental condition in or near the evacuation lumen; and a controller configured to: determine a flow restriction within the evacuation lumen based on reporting from the at least one sensor, and vary the pressure from the pressure source for reduction of the flow restriction based on the determination.

According to some embodiments of the invention, the flow restriction comprises a partial lining of material accumulated on the wall of the evacuation lumen.

According to some embodiments of the invention, the flow restriction comprises a change in the shape of the evacuation lumen.

According to some embodiments of the invention, the flow restriction comprises turbulence in flow through the evacuation lumen.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-3E schematically illustrate sensors and sensing modules of an exemplary colon cleaning system, according to some embodiments of the present invention;

FIGS. 4A-4E schematically illustrate a cleaning system wherein flow of material through the system is blocked by clogs, according to some embodiments of the present invention;

FIG. 4F schematically illustrates a cleaning system, with tables of exemplary sensor readings from sensors within a cleaning system, according to some embodiments of the present invention;

DESCRIPTION OF SPECIFIC EMBODIMENTS OF THE INVENTION

Figure 1:
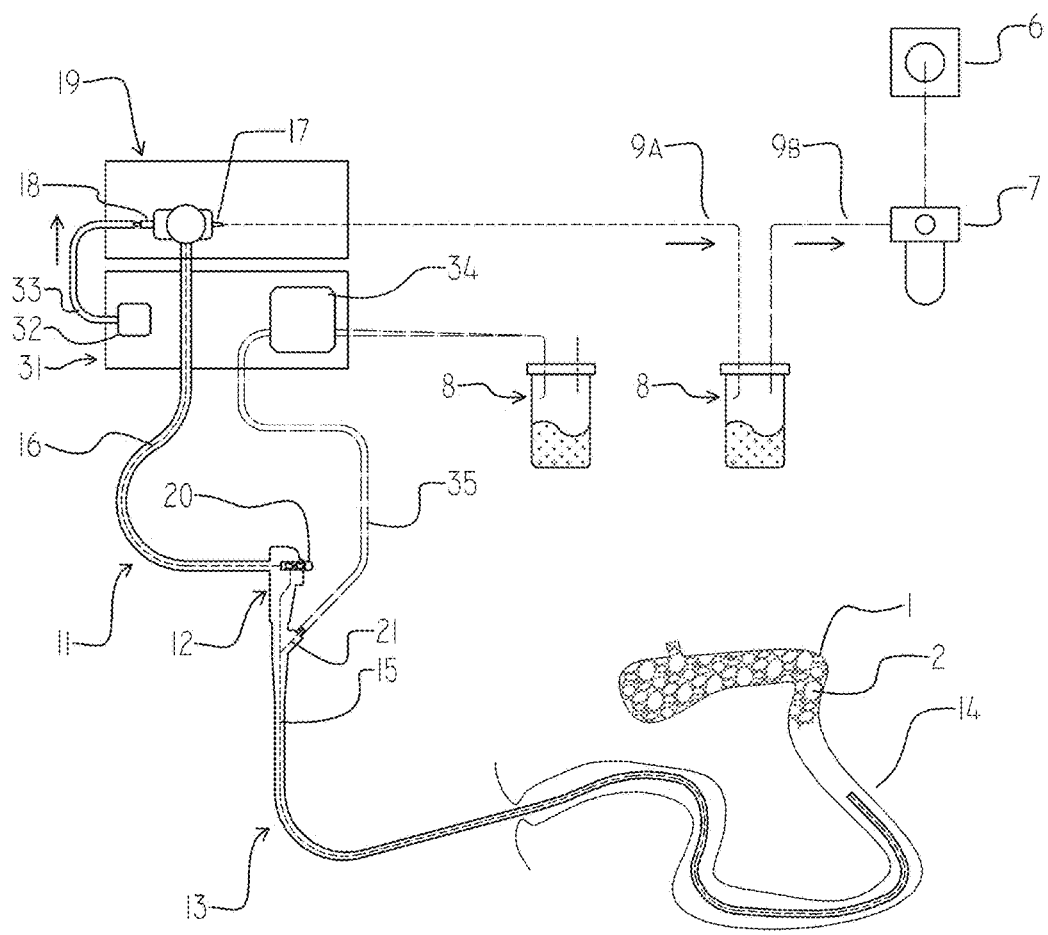
FIG. 1 schematically illustrates an exemplary colon cleaning system comprising a colonoscope workstation and a cleansing workstation, according to some embodiments of the present invention.

The present invention, in some embodiments thereof, relates to a system for cleaning a colon or other body lumen, and, more particularly but not exclusively, to systems and methods for cleaning comprising automated self-cleaning features.

Overview

A broad aspect of some embodiments of the invention relates to tools and techniques for purging an evacuation channel of a cleaning system from fecal or other matter implicated in evacuation channel blockage.

In some embodiments of the invention, one or more irrigating channels transport irrigating material to a distal end of a colon cleaning system. One or more evacuation channels return the material with colon waste. In some embodiments, transport is reversible and/or otherwise variably controllable. Potentially, control of evacuation flow clears or prevents blockages during use with reduced need to interrupt a procedure due to equipment failure.

An aspect of some embodiments of the invention relates to sensors of conditions in a colon cleaning system and/or its operating environment.

In some embodiments of the invention, one or more sensors detect pressure within the bowel or cleansing system. Additionally and/or alternatively, sensors detect another property of material inside or outside the system; for example: flow, flow rate, temperature, conductivity, optical density, spectral properties, pH, and/or osmotic pressure. In some embodiments, sensors monitor system components. Examples include a pump volume meter, a fill level sensor, and/or a valve or intake position sensor.

In some embodiments, distal sensors connect to a workstation by wire or wireless radio. Additionally and/or alternatively, sensors in a workstation sense pressure through one or more sensing ducts with distal outlets.

It is a potential advantage to provide sensors capable of indicating potential and/or recently formed blockages to flow at an early stage of blockage formation. Optionally, blockage comprises blocking material carried by evacuated fluid. Optionally, blocking material comprises a clot. Optionally, blocking material comprises a build-up on an evacuation lumen wall. Potentially, early detection allows initiating action to purge a forming blockage before it becomes an impediment to evacuation function. Potentially, blocking material is more easily purged, the earlier its presence is sensed. Optionally, blockage comprises a restriction in flow due to a change in the shape of an evacuation lumen. The change may be, for example, due to kinking or reduced pressure in an evacuation lumen. Potentially, a change in the pressure exerted in an evacuation lumen reduces the flow restriction. Optionally, a restriction in flow comprises drag due to turbulence in flow. Potentially, a change in the pressure exerted in an evacuation lumen reduces turbulence and associated drag.

An aspect of some embodiments of the invention relates to use of sensed and/or determined system statuses for determining control signals that operate components of a colon cleaning system. Sensing changes during controlled operation optionally allows directed and/or closed-loop control of the system.

In some embodiments of the invention, sensor data are processed to determine a status. Exemplary statuses include channel blockage and bowel pressure. In some embodiments, the determination of blockage in an evacuation channel of the system elicits signaling to operate colon cleaning system components for clearing the block.

For example, a determination of a tip block elicits signaling to terminate suction. Optionally, control signals are modulated based on specifics of a status determination. Determined specifics include, for example: a blockage being full, partial or developing; blockage location; and/or blockage type, for example waste particle or captured tissue.

It is a potential advantage to control actions for purging blockages and potential blockages for reduced interference with evacuation flow. A build-up of material in the colon can slow procedure progress and/or interfere with viewing while purging is completed. Material buildup leading to increased pressure is potentially a danger to the patient.

In some embodiments of the invention, sensing and control have feedback interactions. In one example of feedback, flow direction is cycled in a channel until a determined blockage condition is relieved. In another example, controlled probing pressure changes are commanded. The rate at which they are sensed to propagate through a channel potentially indicates relative volumes of incompressible fluid and compressible gas, and/or flow capacitance. Potentially, this can indicate foaming of evacuating fluid. Parameters of timing, pressure and/or flow control are optionally varied according to this or another actively sensed status. In another example, control signals balance the relative efficacy sensed for two or more subsystems. Optionally, this is useful to balance irrigation volume with evacuation volume.

In some embodiments, a fault status—examples include bowel overpressure, an unremovable blockage, or unexpected sensor values—leads to a control response. Fault responses include, for example: shutting down, pausing, reducing, and/or increasing activity of a system component.

In some embodiments, feedback from sensors is used to control flow in a fluid delivery system which delivers fluid that mixes with fecal matter for evacuation. In some embodiments, the delivered fluid comprises gas, for example, carbon dioxide and/or air. In some embodiments, the delivered fluid comprises a liquid, for example water or saline. In some embodiments of the invention, the supply comprises a mix of gas and water, for example, water and gas jetted together through a fluid supply conduit. In some embodiments, sensing of pressure inside the intestine is used to detect an actual, immanent, developing and/or potentially developing over-pressurization of the intestine (any of which is referred to herein as an overpressure condition). An overpressure condition comprises, for example, a pressure above a safety limit, and/or a changing pressure which appears likely, based on a rate of change, to soon reach a safety limit. In some embodiments, a system reacts to an overpressure condition by reducing a rate of fluid supply, by changing a ratio of gas to liquid in a fluid supply (for example, reducing an amount of gas), and/or by terminating the supply of fluid. In some embodiments, a ratio of evacuation rate to fluid supply is adjusted. Optionally, the fluid supply rate remains fixed while an evacuation rate is increased. In some embodiments of the invention, fluid supply is halted. In some embodiments of the invention, another limit is imposed (additionally or alternatively): for example, a limit to the length of an irrigation sequence. In some embodiments of the invention, a sensor is placed at the distal tip of the cleaning system (where it can be positioned, for example, at the end of an intestine), and outside of the cleaning system lumens, where it is directly exposed to the pressure within the bowel. The sensed pressure is used as a basis for the detection and feedback control of overpressure. In some embodiments, overpressure is controlled by appropriate actions (increase and decrease of material flow) commanded by a controller to balance the input and output of the cleaning device's pressure and/or fluid sources to the colon, while evacuation and irrigation are taking place. In some embodiments, control of irrigation comprises stoppage or reduction of irrigation while purging actions to clear and/or prevent an evacuation lumen blockage take place.

In some embodiments, operator input affects control signals; for example: an onset, duration and/or intensity of irrigation and/or suction. In some embodiments, parameters of device operation include control by a timer, for example, within a preprogrammed cleaning cycle, or as a limiting safety mechanism to protect the bowel from overfilling.

An aspect of some embodiments of the invention relates to the arrangement of the lumenal cross-section area through which evacuation and/or irrigation occur.

In some embodiments of the invention, a plurality of evacuation channels replace a single larger channel. Optionally, a lower maximal probe diameter is allowable thereby for the same overall cross-section. Diameter is a factor in probe flexibility, which in turn may affect colonoscopy procedure completion rates. Potentially, a plurality of evacuation channels allows optional independent operation and/or increased reliability of operation.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

For convenience of exposition, cleaning systems and methods described herein are sometimes referred to as "colon cleaning" systems and methods. Colon cleaning is contemplated as a common use of embodiments of the invention. However, it is to be understood that methods and devices taught herein may also be used to clean other portions of an intestine and/or other body lumens. Accordingly, the term "colon cleaning" as applied to these methods and devices encompasses cleaning not only the colon, but also other portions of an intestine and/or other body lumens.

Reference Embodiment of a Colonoscope Cleaning System

Reference is now made to FIG. 1, which schematically illustrates a colon cleaning system comprising colonoscope work station 19 and a cleansing work station 31, according to some exemplary embodiments of the invention.

In some exemplary embodiments of the invention, the colonoscope and cleansing work stations 19, 31 connect via water or gas pipe 33. Optionally, pipe 33 connects at one end to the water or gas pump 32 of cleansing work station 31, and at the other end to colonoscope 19 water or gas inlet 18. Optionally, colonoscope umbilical cord 11 comprises internal tubes 16. Colonoscope insertion tube 13 connects to colonoscope umbilical cord 11 via colonoscope handle 12. In some embodiments, handle 12 comprises vacuum valve 20 and work channel inlet 21. Colonoscope tip 14 is depicted navigating through a colon 1 full of fecal matter 2.

In some exemplary embodiments, cleansing work station pump 34 connects via pipe 35 to colonoscope work channel 21 at one end, and to fluids container 8 at the other end. In some embodiments, colonoscope vacuum inlet 17 connects via fluid line 9A to fluid container 8. Optionally, suction wall pump 6 connects through a regulator 7 via lines 9B to container 8.

In some embodiments of the invention, operating pump 32 augments irrigation of the colon with a supply of gas and/or water through pipe 33 and inlet 18 to colonoscope work station 19. In some embodiments, irrigation material is supplied via internal pipes 16 and working channel 15 all the way to colonoscope tip 14, augmenting cleaning colon 1 of fecal matter 2. In some embodiments of the invention, supplied gas comprises, for example air or carbon dioxide.

In some embodiments of the invention, fecal matter is evacuated through colonoscope working channel 15 and internal pipes 16 through vacuum inlet 17. Optionally, inlet 6 provides lowered pressure via regulator 7 through pipe line 9B and 9A to suck fecal matter into fluids container 8.

In some embodiments, evacuation is augmented as needed by cleansing working station 31. Optionally, operating pump 34 and/or opening inlet 21 creates pressure differentials which move material through pipe 35 into fluids container 8.

According to the embodiment of the invention, colon cleaning systems comprise colonoscopes or are parts of colonoscopes. Alternatively and/or additionally, some embodiments presented herein may be implemented as cleaning systems independent of and optionally usable with colonoscopes.

In some embodiments of the invention, some components are provided by a colonoscope with which a colon cleaning system is used. For example, a cleaning system according to some embodiments of the invention uses a working channel of a colonoscope as an irrigation channel and/or as a matter evacuation channel (also described herein as an evacuation lumen). In some embodiments, components are provided separately from the colonoscope. For example, a cleaning system according to some embodiments of the invention uses channels or other tools external to a colonoscope as irrigation channels, evacuation channels and/or other system components.

Sensors and Motive Devices for Exemplary Cleaning Systems

Figure 2A:
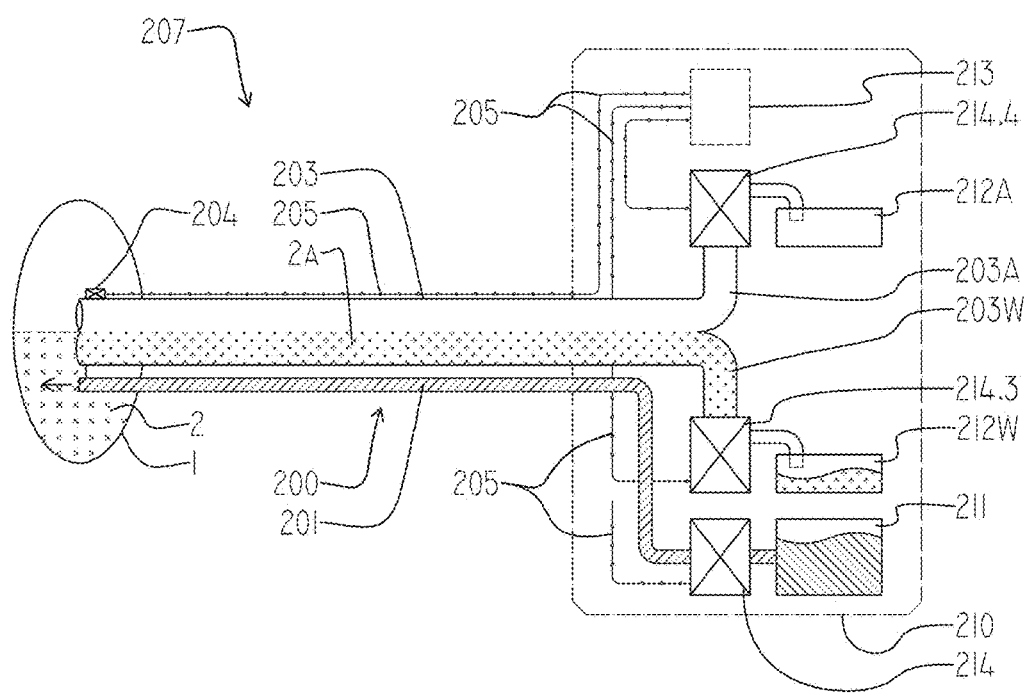
FIGS. 2A-2D schematically illustrate sensors and sensing modules of an exemplary colon cleaning system, according to some embodiments of the present invention.

Reference is now made to FIG. 2A, which schematically illustrates a colon cleaning system 207 with sensors in accordance with some exemplary embodiments of the present invention.

In some embodiments of the invention, cleaning system 207 comprises one or more motive devices for moving fluid through channels (for example, pumps 214, 214.3, 214.4). Optionally, motive devices are operated from signals sent by a controller 213. Optionally, controller 213 determines controlling signals based on inputs from one or more sensors 204.

In some embodiments of the invention, cleaning system 207 comprises an insertable portion 200 insertable to colon 1 of a patient, and external work station 210. In some embodiments, system 207 comprises an irrigation pipe 201 through which an irrigation fluid such as water and/or other liquid may be provided into colon 1. Irrigation pipe 201 is connectable to a source of water or other liquid 211.

Exemplary Motive Devices

System 207 optionally comprises one or more waste collection devices 212A, 212W for collection of waste matter (including fecal matter) evacuated from colon 1. System 207 optionally comprises an evacuation pump 214.3, 214.4 which provides suction for evacuating matter from colon 1 through system 207. During some phases of a colon cleaning operation, pump 214.3, 214.4 evacuates fecal matter (optionally loosened and/or transported by liquid from irrigation pipe 201) from colon 1 into waste collection device 212A, 212W via an evacuation channel 203.

In some embodiments of the invention, evacuation pump 214.3, 214.4 is external to the device. Optionally, evacuation pump 214.3, 214.4 is a connection to a vacuum supplied by a distant pump, such as is available from a vacuum source connector available in many hospitals and clinics. In this case, references herein to controlling pump 214.3, 214.4 (e.g. starting and stopping its suction-creating operation) may be understood to refer to controlling a valve connecting an evacuation tube of a cleaning system to such a distant vacuum source.

In some embodiments of the invention, system 207 comprises a pressure sensor 204, positioned on or near a distal end of evacuation channel 203, for measuring pressure in colon 1. In some embodiments, sensor 204 reports pressure readings to a controller 213. Optionally, controller 213 controls operation of one or more of pumps 214, 214.3 and/or 214.4. Control of operation comprises, for example, starting, stopping, and/or modifying the speed or power of a pump 214, 214.3, 214.4. Optionally, control of operation is based on pressure readings detected at sensor 204.

In some embodiments, controller 213 comprises a processor for calculating and sending commands to pumps 214, 214.3, 214.4 based on and/or as a function of sensor readings from sensor 204. Optionally, control is based on other sensing mechanisms and/or inputs in system 207, for example commands input by a user.

In some embodiments, system 207 comprises a purge pump 214 for inputting water and/or other fluid to system 207. Optionally, system 207 comprises a fluid source 211 of, for example: water, another liquid, a mixture of liquid and gas, and/or gas such as pressurized air or carbon dioxide. Optionally, purge pump 214 introduces fluid under pressure to purge portions of system 207 such as evacuation channel 203. Purging is activated, for example, when a blockage of evacuation channel 203 is determined by controller 213 based on input from sensor 204 or another source. According to the embodiment, controller 213 controls pumps 214, 214.3, 214.4 via wired or wireless connections 205.

In some embodiments of system 207, some or all of controller 213, purge pump 214, evacuation pump 214.3, 214.4, and waste collection device 212W are grouped together in a work station 210.

Exemplary Sensor Locations

In FIG. 2A, exemplary sensor 204 is shown positioned at a distal end of evacuation channel 203 and external to that channel. Sensor 204 in this position directly measures pressure within colon 1 when channel 203 is inserted in colon 1. In some embodiments of the invention, sensor 204 is an electronic pressure sensor.

Figure 2B:
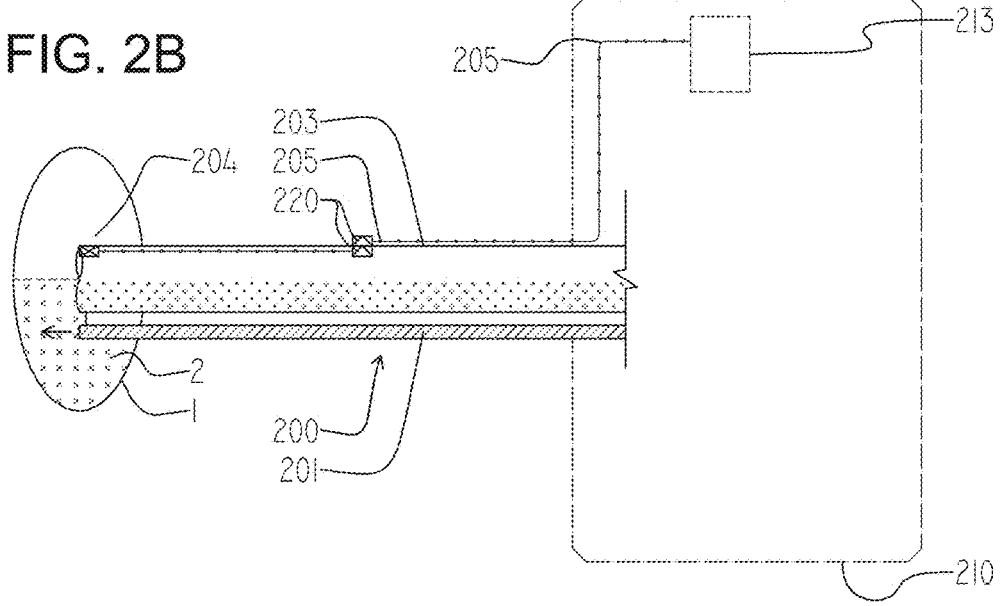
Figure 2C:
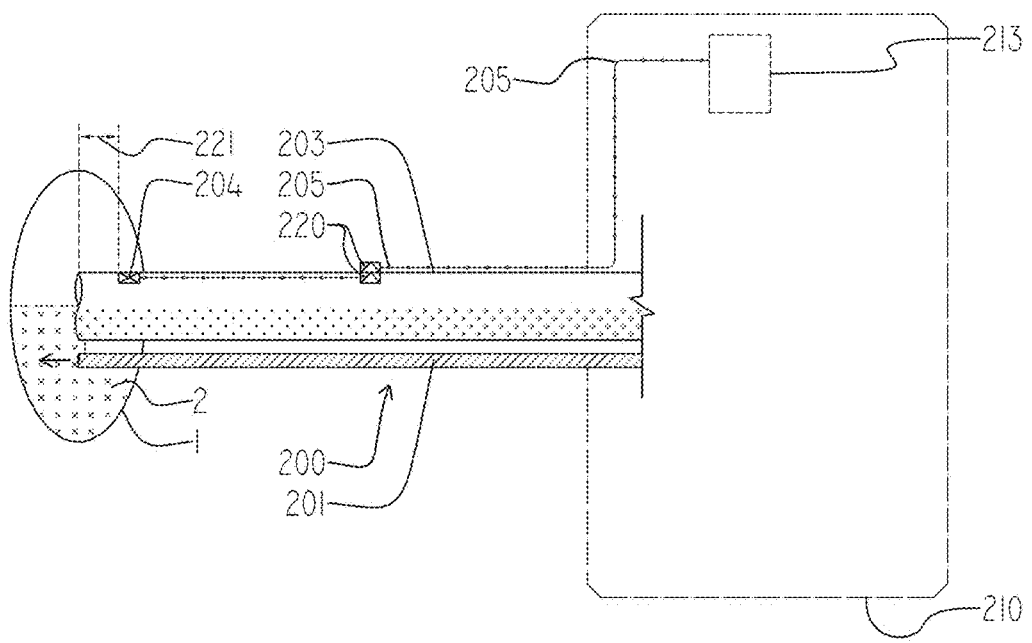
Figure 2D:
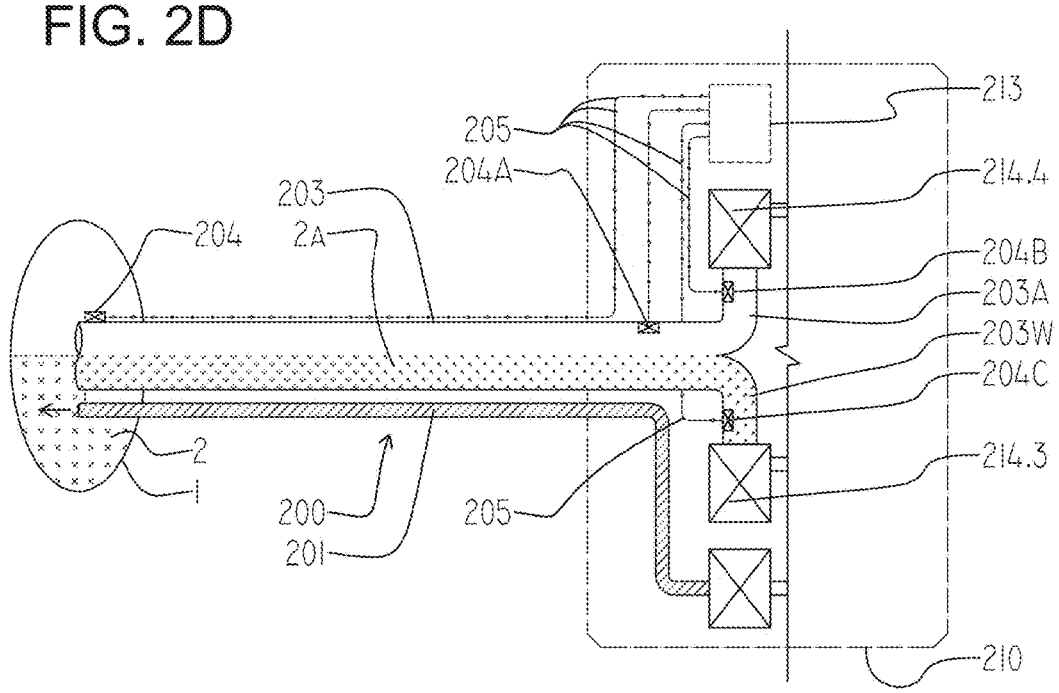

Reference is now made to FIGS. 2B-2D, which schematically illustrate additional or alternative sensor placement positions within a cleaning system 207 such as that of FIG. 2A, according to some exemplary embodiments of the invention.

In FIG. 2B, exemplary sensor 204 is positioned at or near a distal end of channel 203 and inside channel 203. In this configuration, sensor 204 measures and reports pressure within a distal portion of channel 203. Optionally, sensor 204 is connected by a wired connection 205 through a connector 220 to controller 213. In some embodiments of the invention, a wired connection 205 runs inside channel 203 along all or part of its length. The connection transfers outside of channel 203 (for example, through a connector 220) at a point proximal to the portion of channel 203 inserted into a colon during use. In some embodiments of the invention, connector 220 is an electrically conductive connection. In some embodiments of the invention, the connection is wireless; for example, a radio or optically coupled connection.

In FIG. 2C, exemplary sensor 204 is positioned within evacuation channel 203 and at a distance 221 from a distal end of channel 203. According to the embodiment, distance 221 is, for example, 0 mm, 1 mm, 2 mm, 5 mm, 10 mm, 20 mm, 30 mm, any distance in between, or a larger or smaller distance.

In FIG. 2D, exemplary sensors 204A, 204B, 204C are positioned at or near a proximal end of channel 203. Three sensors are shown: one 204A at a proximal end of channel 203, one 204B in a sub-channel connecting evacuation pump 214.4 to channel 203, and one 204C in a sub-channel connecting purge pump 214.3 to evacuation channel 203. Optionally, sensor 204 is placed outside channel 203. Potentially, this allows sensing of pressure directly within the bowel. This is a potential advantage, for example, to allow pressure to be sensed such that over-pressurization of the bowel can be prevented. Prevention of over-pressurization is, for example, by termination and/or reduction of the delivery of gas or fluid to the bowel (for example, by irrigation pipe 201). In some embodiments, delivery by irrigation pipe 201 (which is optionally a jetting delivery system), or another gas or fluid delivery system, such as an insufflation tube to maintain bowel inflation, is reduced and/or terminated when pressure is determined to be at, near, and/or nearing (rising to approach) an over-pressure condition. In some embodiments, pressure rising to approach over-pressure is determined on the basis of a difference of pressure measured during at least two different times. Additionally or alternatively, evacuation rate is increased at or near a sensed over-pressure condition. Potentially this prevents over-inflation, while allowing cleaning to continue uninterrupted.

In some embodiments of the invention, sensor placements shown in FIGS. 2A-2D and/or other figures herein are combined. In some embodiments of the invention, for example, a single sensor 204 is positioned at a position as shown in one of FIGS. 2A-2D. In some embodiments, a plurality of sensors are positioned at a position shown, for example for redundancy. Additionally and/or alternatively, sensors may be positioned at a plurality of positions as shown.

Exemplary Sensor Devices

Figure 3A:
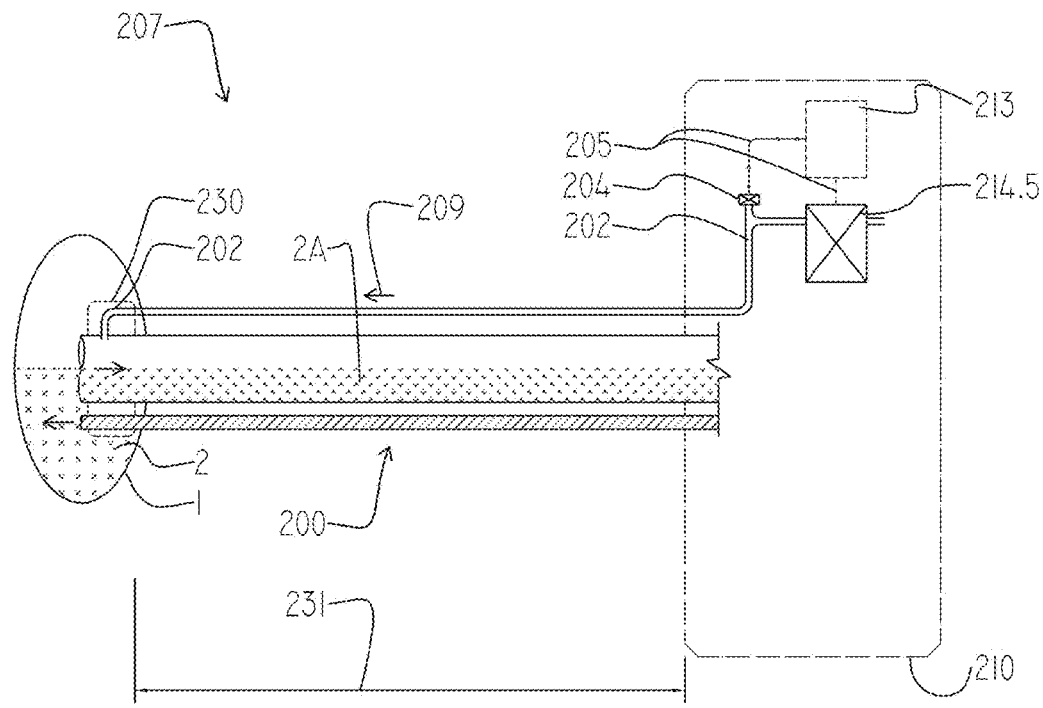
Figure 3B:
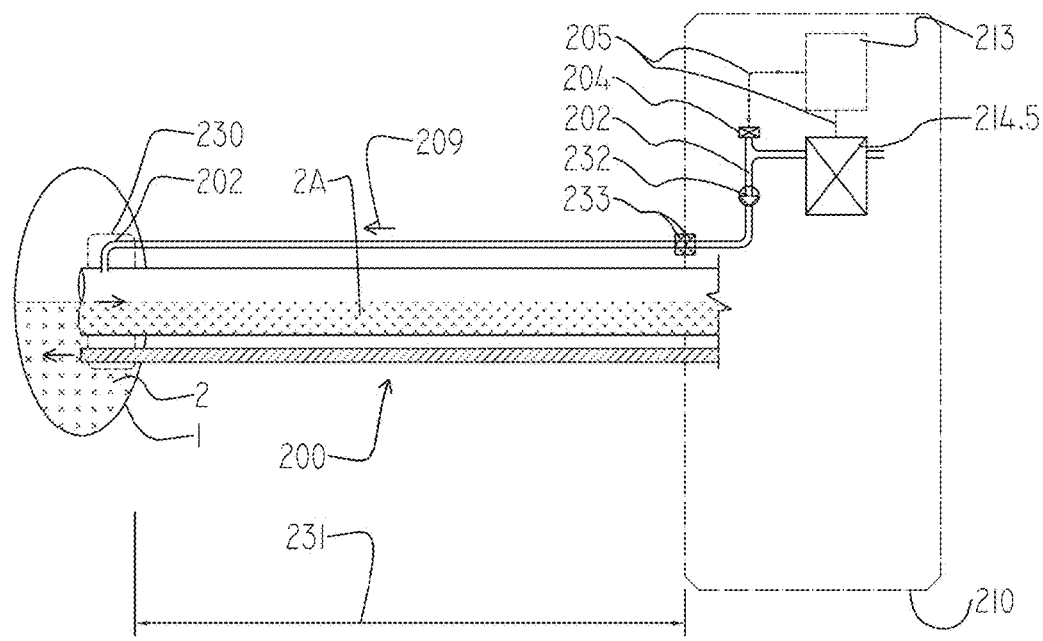

Reference is now made to FIGS. 3A-3B, which schematically illustrate a colon cleaning system 207 including a remote pressure-sensing sensing module, in accordance with some exemplary embodiments of the present invention.

In some embodiments of the invention, pump 214.5 is actuatable to generate positive pressure in tube 202, extending from pump 214.5 to a distal end of evacuation channel 203. Optionally, pump 214.5 is positioned within work station 210. Optionally, tube 202 is connected to evacuation channel 203 via a head device 230. The working fluid pumped by pump 214.5 is, for example, air, carbon dioxide, water, or another fluid.

Positive pressure potentially produces flow 209 in tube 202. During colon cleaning, suction provided by an evacuation pump (not shown) causes flow 209 to enter the distal end of evacuation channel 203. From there, it is drawn the length of channel 203 and out of system 207.

While flow 209 continues uninterrupted, pressure buildup in tube 202 and channel 203 is avoided. A flow or pressure sensor 204 senses pressure or rate of flow 209 and reports to controller 213.

In some embodiments of the invention, when a clog or obstruction blocks or partially blocks evacuation channel 203, flow is not exhausted or is inefficiently exhausted from channel 203. Pressure builds and/or flow slows in channel 203 and/or tube 202. Pressure/flow sensor 204 detects a change.

In some embodiments, the sensor 204 reports a change and/or a changing value to controller 213. In some embodiments, controller 213 determines the existence of a blockage from a detected drop in flow or increase in pressure. Optionally, controller 213 initiates corrective action to eliminate the blockage and restore flow 209, as detailed in relation to, for example, FIGS. 4A-4F and 5A-5C.

A potential advantage of a configuration using remote sensing is that sensors and associated electronics occupy portions of system 207 outside the body. Potentially, this reduces regulatory concerns over the introduction of electronic devices to a body cavity. The length of tube 202 may be, for example, more than 2 m, 3 m, 4 m, or any length in between.

Figure 3C:
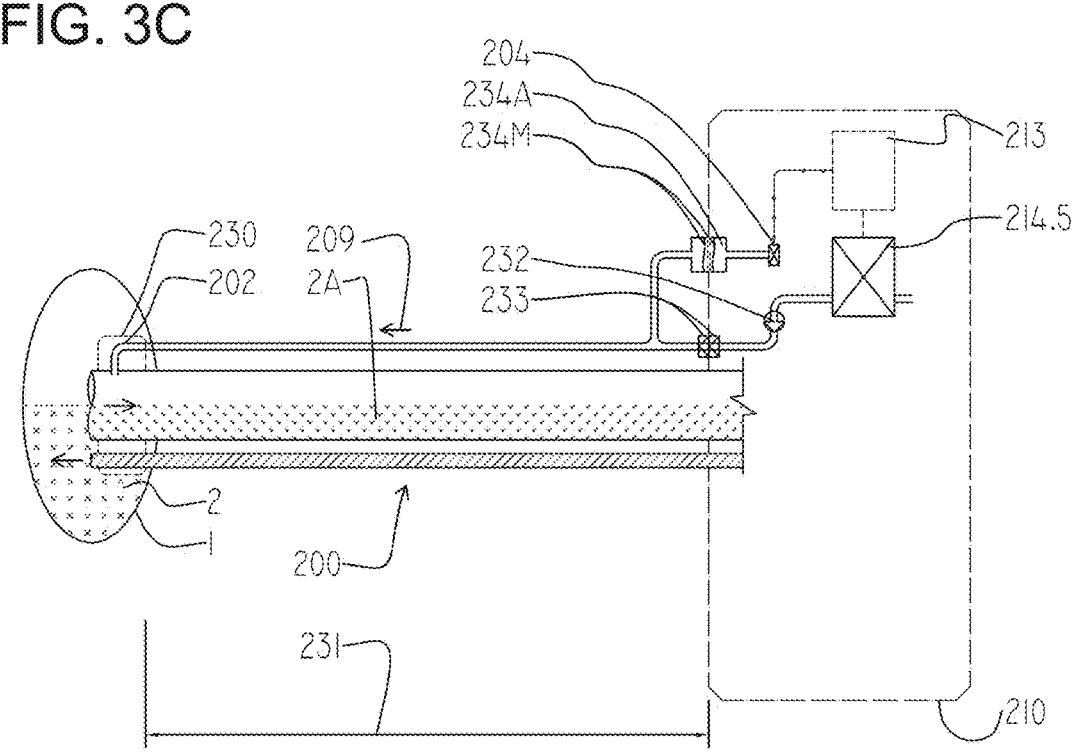

Reference is now made to FIG. 3C, which schematically illustrates a variation of a sensing module for colon cleaning system 207, according to some exemplary embodiments of the invention.

It is a potential advantage to prevent fault conditions from contaminating the interior of the cleaning system.

In some embodiments of the invention, sensor 204 is protected from potential backflow into tube 202 by a protective membrane 234M which comprises a barrier to backflowing material. In some embodiments, membrane 234M is sufficiently flexible that pressure changes are communicated across it to chamber 234A where sensor 204 is located.

In some embodiments of the invention, a check valve 232 resists backflow through coupler 233. If back pressure overcomes the forward pressure of pump 214.5, the valve closes, preventing flow from passing across connector 233 and contaminating the system.

Figure 3D:
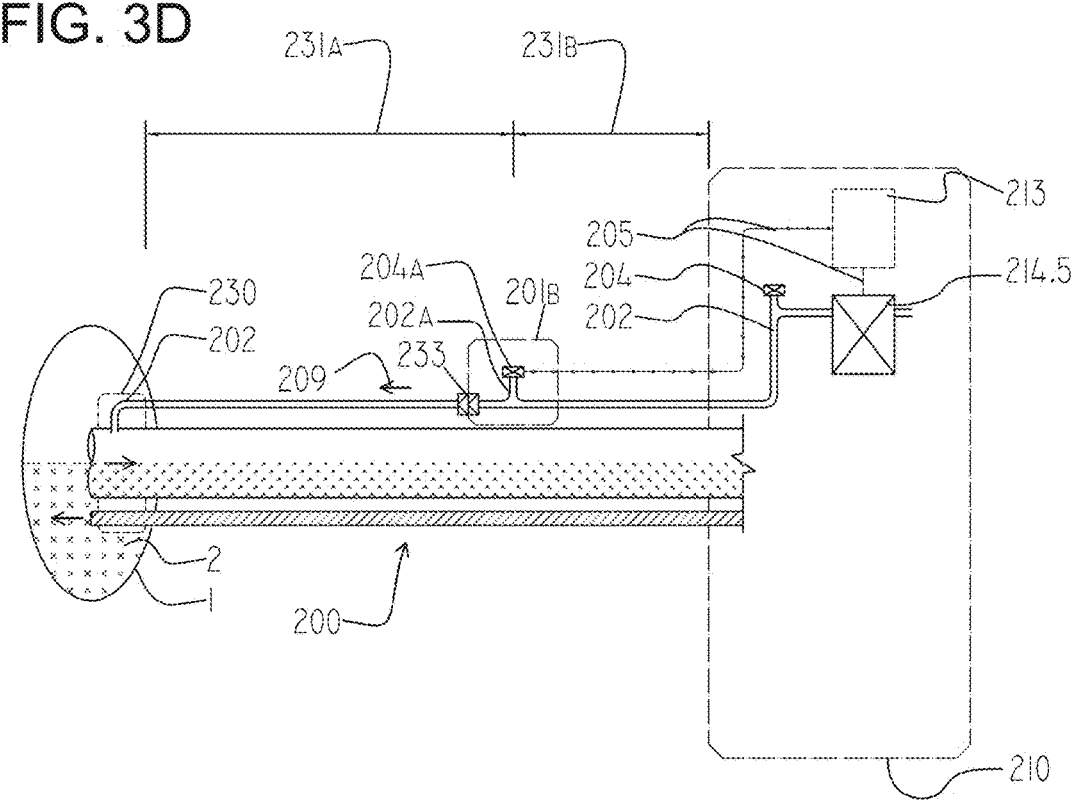

Reference is now made to FIG. 3D, which schematically illustrates a variation of a sensing module for colon cleaning system 207, according to some exemplary embodiments of the invention.

In some embodiments of the invention, flow provided by pump 214.5 and flowing through tube 202 is measured by sensor (pressure and/or flow meter) 204A, distal to sensor 204. Optionally, sensor (pressure and/or flow meter) 204A is mounted in an independent work station 201B. From there, it connects through a connector 233 and an additional flow tube 202A to an outlet in a distal portion of evacuation channel 203.

A potential advantage of this embodiment is reduction of the distance 231A between the sensor 204A and the distal outlet of tube 202 in channel 203. The reduced distance is shorter than the sum of the distances 231A and 231B. Potentially, therefore, pressure and/or flow readings from sensor 204A will respond more accurately to blockages in channel 203, producing more accurate sensor readings.

Reference is now made to FIG. 3E, which schematically illustrates a variation of a sensing module for colon cleaning system 207, according to some exemplary embodiments of the invention.

In some embodiments of the invention, flow provided by pump 214.5 and flowing through tube 202 is measured by sensor (and/or flow meter) 204A, distal to sensor 204. Optionally, sensor (and/or flow meter) 204A is mounted in an extension 240 of work station 210. Sensor 204A connects through a connector 233 to an outlet in a distal portion of evacuation channel 203.

A potential advantage of this embodiment is shortened distance 241A between the sensor 204A and the distal outlet of tube 202 in channel 203. The distance is shortened relative to the sum of the distances 241A and 241B. Potentially, therefore, pressure and/or flow readings from sensor 204A will respond more accurately to blockages in channel 203, producing more accurate sensor readings.

FIGS. 2A-3E illustrate placements of sensors, described hereinabove in connection to exemplary sensor types and configurations, including pressure sensing and flow sensing. In some embodiments of the invention, sensors of one or more alternative types detect another parameter related to material inside or outside the system. Examples include: flow rate, particle sensing, temperature, conductivity, optical density, spectral properties, pH, and/or osmotic pressure. In some embodiments of the invention, a probe energy source appropriate to the sensor type, for example a source of illumination for an optical probe, is appropriately disposed.

According to the embodiment, sensor types relate to the operation of a colon cleansing system in the following exemplary aspects:

A flow rate sensor determines flow by velocity rather than volume. A low flow rate potentially indicates a blockage, for example, in the lumen of an evacuation channel.

A particle sensor provides information on particles within a sensing region. According to the embodiment, a particle sensor is used, for example: to provide a rate of particle motion, potentially indicating a blockage; to provide particle size estimation, potentially indicating a need for more energetic breaking of particles and/or an increased risk of blockage; and/or to provide a count or estimate of particle density, potentially indicating an increased risk of blockage.

A temperature sensor provides a temperature within a sensing region. Sensed changes in fluid temperature potentially indicate, for example, a longer or shorter dwell time of fluid in the body. Optionally, dwell time in the body is indicated by the amount to which an irrigation fluid temperature, beginning at a temperature different from body temperature, has equilibrated to human body temperature. Potentially, information on fluid dwell time assists a determination of net flow in the system.

A conductivity sensor provides an indication of electrical conductance, for example the conductance of evacuating waste fluids. A change in conductance potentially indicates, for example: a change in the relative mixture of gas and fluid in evacuated discharge (including indicating foaming and/or the evacuation of substantially all fluid) and/or a change in the balance of irrigating fluid and bowel fluid in the evacuation channel.

A pH sensor provides an indication of ionic concentrations in a fluid. A change in pH potentially indicates, for example, a change in the balance of irrigating fluid and bowel fluid in the evacuation channel.

An osmotic sensor provides an indication of solute concentration in a fluid. A change in solute concentration potentially indicates, for example, a change in the balance of irrigating fluid and bowel fluid in the evacuation channel.

An optical density sensor provides an indication of the optical density of a fluid. Measurement of optical density (and in particular turbidity) potentially provides, for example, an indication of the waste content of evacuated waste fluid, and/or foaming in the fluid. A range of optical densities is potentially an indication of a greater potential for a blockage to develop. In particular, such a range may be set at the low end by a relative lack of particles in a channel, and at a high end by turbidity sufficient to indicate that particles are small and unlikely to form blockages. Additionally or alternatively, a high optical density is potentially an indication of foaming.

A spectral sensor indicates light spectral properties, for example, optical density as a function of light wavelength. Measurement of spectral properties potentially reveals the concentrations of one or more substances in evacuated irrigation matter. Optionally, illumination, sensing, and processing are tuned to the properties of hemoglobin. Potentially, sensed hemoglobin in evacuated irrigation material provides an indication of hemorrhaging, a serious complication in a small proportion of colonoscopy procedures. In some embodiments, a foaming fluid, dominated by scatter having spectral properties similar to the illumination light, is distinguishable from a particle-laden fluid, having spectral properties which absorb light according to the particle content.

Sensing of pump operation and/or pumping efficacy parameters (for example, of a rate of rotor rotation, or of acceleration) potentially provides an indication, for example, of the density of material the pump is moving. Potentially, reduced density of the material indicates foaming.

Exemplary Blockage Removal

Reference is now made to FIGS. 4A-4D, which schematically illustrate removal of blockages from an evacuation channel 203 of a colon cleaning system, according to some exemplary embodiments of the invention.

During cleansing, pump 214 supplies irrigation liquid from fluid container 211 via tube 201 to the colon 1, while pump 214.3 evacuates fecal matter 2 combined with irrigating fluid 2A via tube 203 into collecting container 212W.

Figure 4A:
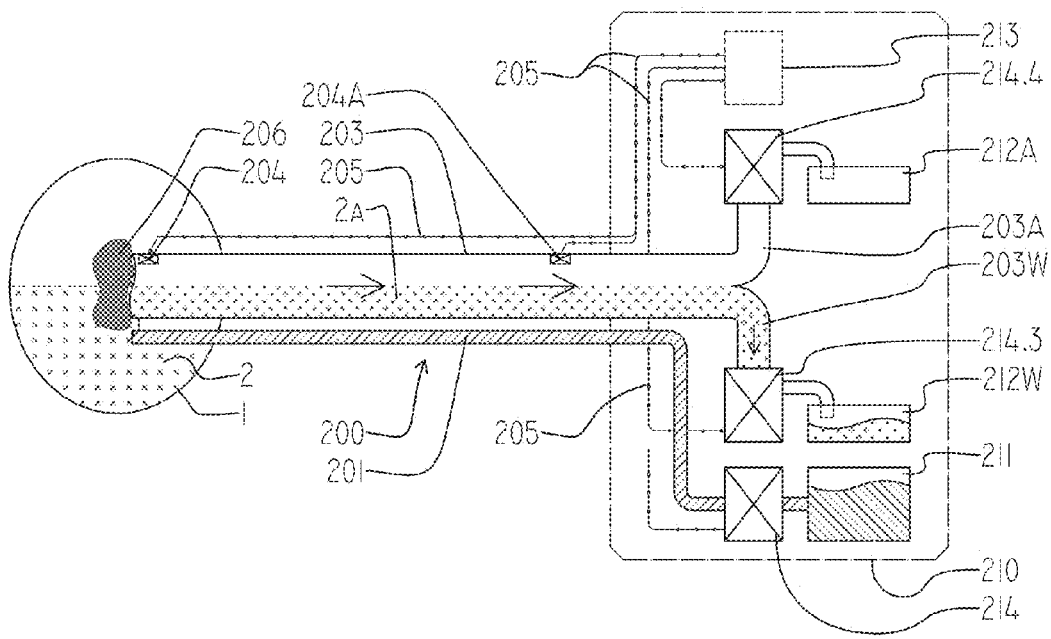

In FIG. 4A, evacuation channel 203 is blocked or partially blocked by fecal matter 206 covering an intake aperture. In FIG. 4C, evacuation channel 203 is blocked or partially blocked by fecal matter 206 lodged and/or wedged inside.

When there is blockage of tube 203, pressure sensors 204 and/or 204A read changes in pressure level, and signal those changes to controller 213, for example via wire 205. Based on the sensed data, controller 213 potentially makes a determination that a blockage exists.

Figure 4B:
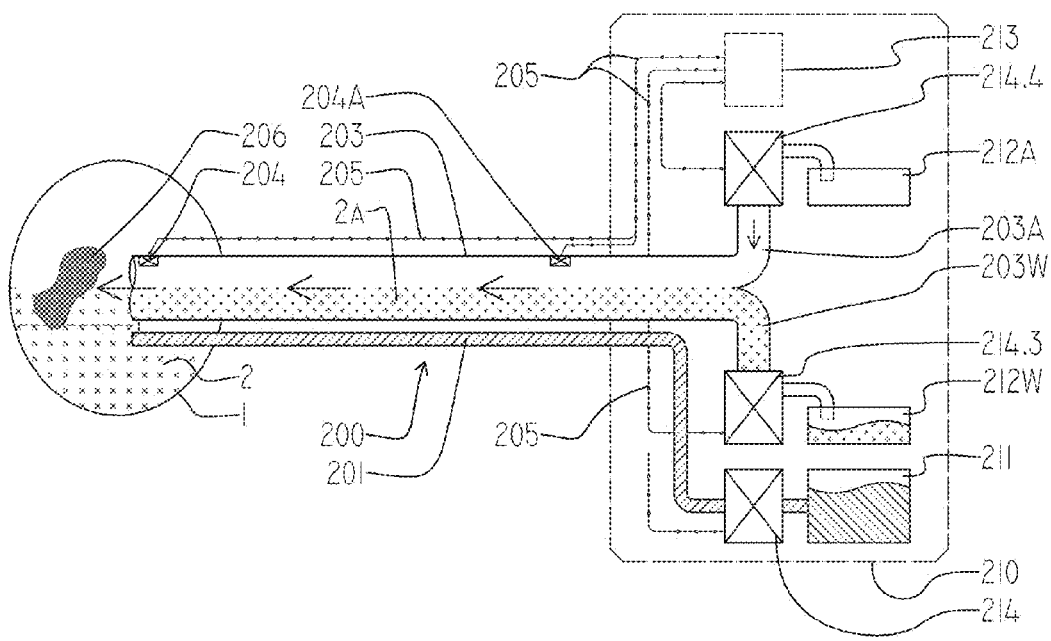

Having determined that a blockage exists, controller 213 stops pump 214, 214.3 operation and starts operation of pump 214.4. Pump 214.4 supplies liquid from container 212A into evacuation tube 203 under reversed pressure, potentially pushing a developed or developing blockage 206 away (FIGS. 4B and 4D).

It should be noted that as evacuation channel 203 is inserted into an intestine, it potentially acquires constrictions and/or partial collapses. Narrowed portions potentially result, for example, from twists of channel 203 imposed by colon anatomy and/or colon position, and/or from body organs or other objects pressing on channel 203. These narrowed portions tend to catch and hold large pieces of passing fecal matter at the point where they are too large to pass. Potentially, therefore, fecal matter 206 is primarily blocked in one direction of travel, and susceptible to backward expulsion from regions which it has reached and cannot pass. The blockage is particularly susceptible to backward expulsion if corrective action is taken before there is a chance for it to become impacted from behind by following particles.

Reference is now made to FIGS. 4E-4F, which schematically illustrate details of how clot material positioning in or on channel 203 affects readings of exemplary system sensors 204, 204A, 204B, according to some exemplary embodiments of the invention. Also given are sets of exemplary sensor readings 250, 251, 252, 253, used in determination of status by controller 213.

The exemplary system sensors comprise pressure sensors in distal, proximal, and medial portions of a channel 203—sensors 204, 204B, and 204A, respectively. Sensor types are exemplary, and could be different according to the embodiment.

Sensor reading set 250 reflects the status of a system which is not flushing, evacuating, or purging. Flowmeter 204A shows zero flow, and pressure sensors 204 and 204A and 204B report zero difference from ambient pressure. A flow meter, if present (for example at the location of 204A), would indicate no flow.

Sensor reading set 253 comprises exemplary readings reflecting the status of a system where normal evacuation flow is occurring during colon cleaning. Sensors 204, 204A, and 204B read −10 mbar, −200 mbar and −300 mbar respectively relative to ambient pressure. A flow meter, if present, would indicate flow.

Two exemplary abnormal situations are also shown.

Sensor reading set 251 comprises exemplary sensor readings reflecting the status of a system in which fecal matter 206 (FIG. 4E) clogs the tip of evacuation channel 203. Sensors 204, 204A, 204B all read a low pressure of −300 mbar relative to ambient pressure. A flow meter, if present, would indicate no flow.

Sensor reading set 252 comprises exemplary sensor readings reflecting the status of a system in which fecal matter 206 (FIG. 4F) clogs the interior of evacuation channel 203. Sensors 204, 204A, and 204B read −10 mbar, −300 mbar and −300 mbar respectively relative to ambient pressure. A flow meter, if present, would indicate no flow.

Blockage potentially begins as a partial occlusion, developing over time into greater occlusion and/or increased resistance to purging. In some embodiments of the invention, sensing is performed at a sufficient frequency to detect intermediate pressure values between a blocked and an unblocked state. The sampling rate is, for example, 5 Hz, 10 Hz, 20 Hz, 50 Hz, 100 Hz, 200 Hz, a frequency in between, or a higher or lower frequency. In some embodiments of the invention, the detection of intermediate pressure values allows determination that a blockage is in development. The determination is potentially before the blockage begins to significantly impair the flow of evacuation fluid. In some embodiments of the invention, the determination is before a blockage reaches a particular threshold of flow impairment, for example 10%, 20%, 40%, 50%, 80%, or another higher or lower threshold of flow impairment. In some embodiments of the invention, the determination is within a particular time interval after reaching a particular threshold of flow impairment, for example: within 10-20 msec after reaching at least 90-95% occlusion, within 15-40 msec after reaching at least 85-95% occlusion, within 25-50 msec after reaching at least 70-80% occlusion, within 50-100 msec after reaching at least 50% occlusion, or within 50-100 msec after reaching at least 90% occlusion. A potential advantage of early detection of a developing blockage is that action can be taken to purge the evacuation lumen before the blockage becomes securely wedged in place. Potentially, a small obstruction (for example, of 15% of the lumen diameter), begins a chain-reaction leading to a full blockage: for example, a 90%-of-lumen-diameter particle, which previously passed freely, is potentially impeded upon encountering a 20%-of-lumen-diameter blockage, becoming itself an obstruction. At this stage, even if occlusion already approaches 100%, the blockage is potentially reversed more easily if detection is rapid, as additional particles coming from behind may add to the developing block, increasing its resistance to purging.

Another potential advantage of early detection of a developing blockage is that the action required to dislodge a small block can be less aggressive, so that interference with cleaning and evacuation is less interfered with.

Figure 5A:
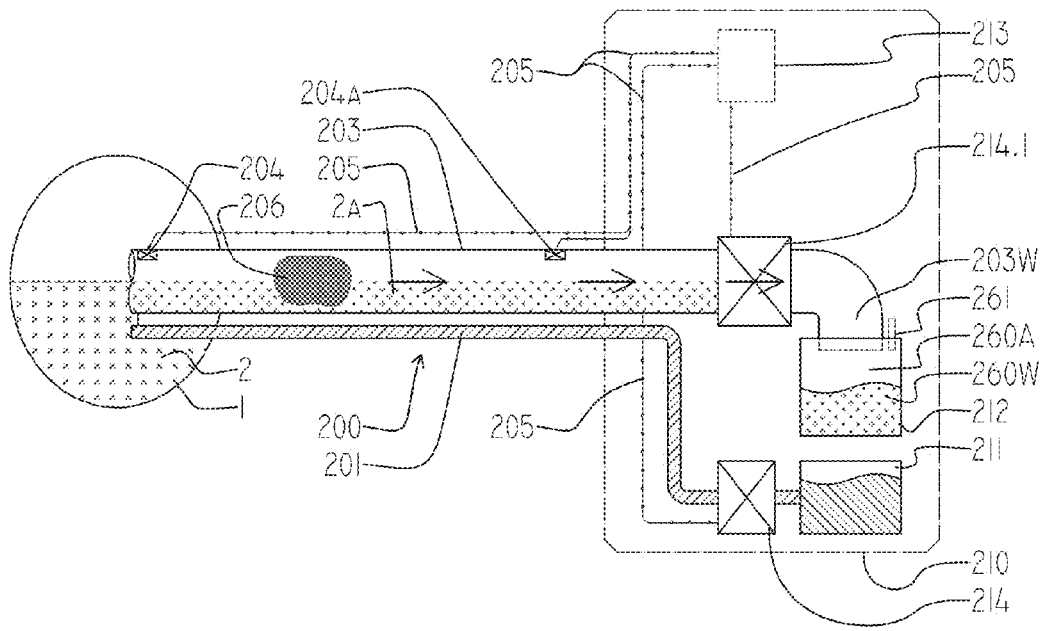
FIGS. 5A-5C schematically illustrate a cleaning system comprising a bi-directional pump, wherein flow of material through the system is blocked by clogs and then purged, according to some embodiments of the present invention.
Figure 5B:
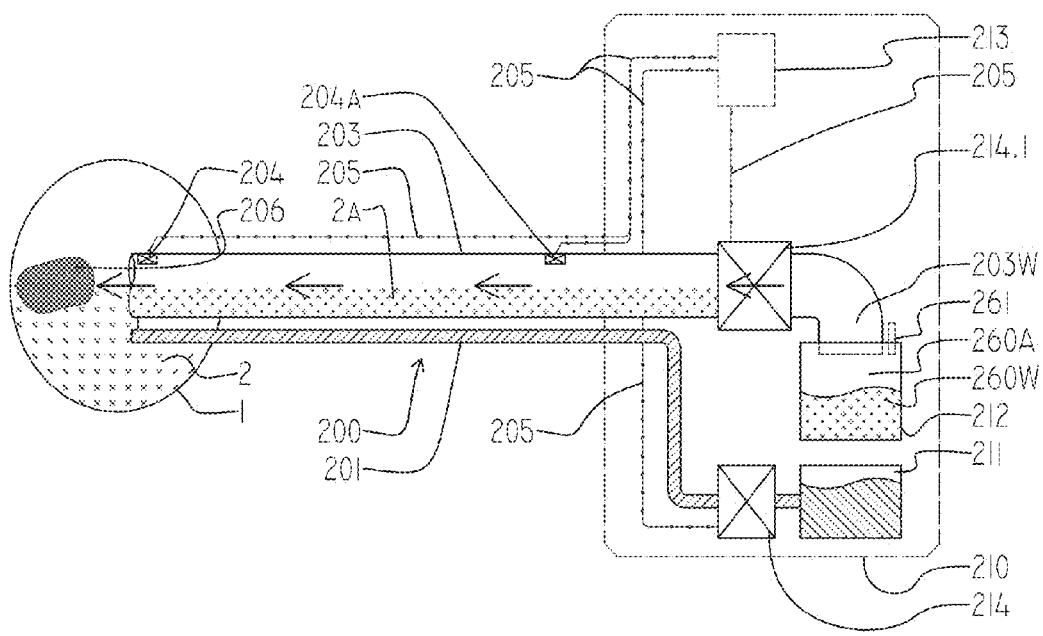
Figure 5C:
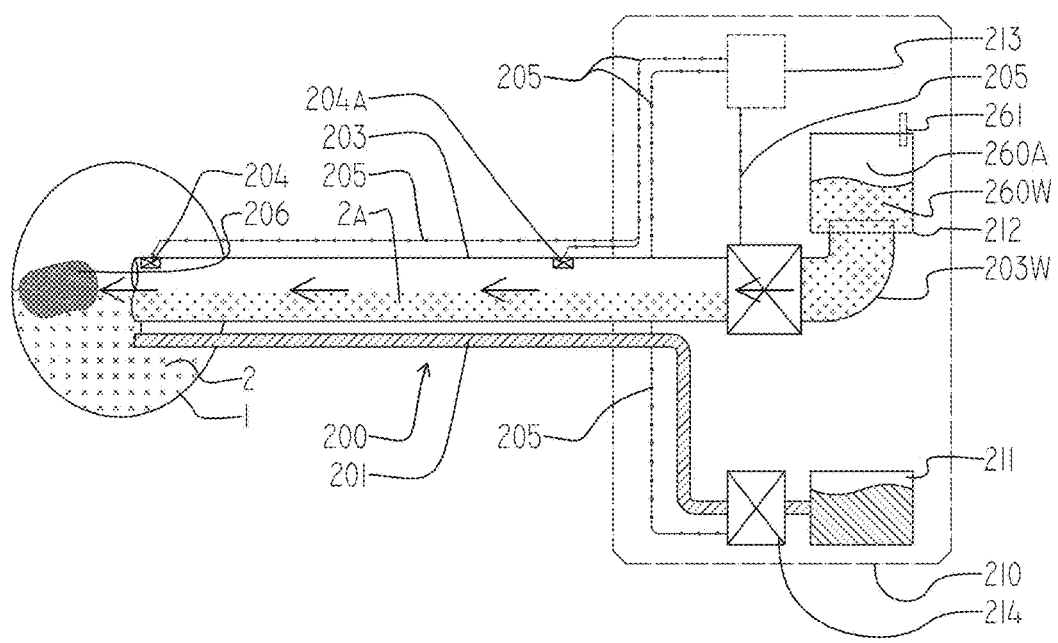

Reference is now made to FIGS. 5A-5C, which schematically illustrate a single pump 214.1 operable as an evacuation and purging pump, in accordance with exemplary embodiments of the invention.

In some exemplary embodiments of the invention, pump 214.1 has bi-directional pumping capability to pump material in both distal and proximal directions, according to its mode of operation.

In some exemplary embodiments, pump 214.1 pulls waste proximally to evacuate it during an irrigation phase of colon cleaning. In some embodiments, upon a determination to purge evacuation channel 203, controller 213 reverses the pumping direction of pump 214.1, producing distal-acting pressure, and possibly flow. The determination is, for example, in response to a determined blockage 206 as in FIG. 5A and/or a user's manual command. The distal-acting pressure and/or flow pushes against a determined blockage 206, potentially dislodging it from within channel 203 (FIG. 5B or 5C).

Optionally, the purging pulse is brief, for example, 50 msec, 100 msec, 200 msec, 500 msec, 1000 msec, 2000 msec, any time in between, or a larger or smaller time. It is a potential advantage to keep purging no longer than necessary to dislodge a blockage, to avoid pushing large quantities of material back into the colon. Optionally, alternating pulses of suction and purging are delivered. The total pulse number is, for example: 2 pulses, 4 pulses, 8 pulses, 20 pulses, 40 pulses, 80 pulses, any number in between, or a larger or smaller number of pulses. It is potential advantage to deliver a sequence of pulses, to agitate and/or batter blocking matter. Potentially, a sequence of pulses breaks apart clumps, unblocking the channel.

In some embodiments, the purging material container 212 contains both gas 260A and fluid 260W. In some embodiments, tube 203W is positionable to selectively pull in either gas 260A or fluid 260W during a purging operation. For example, tube 203W in FIG. 5B is pushed down into fluid 260W to extract fluid, or raised into gas (for example air) 260A to extract gas. Optionally, container 212 is invertible, for example, held in the hands. Holding container 212 as in FIG. 5B allows, for example, gas 260A to be extracted for purging. Inverting container 212 as in FIG. 5C allows fluid 260W to be extracted for purging.

In some embodiments, a vent 261 on container 212 allows accumulated gas to be vented, and/or to be drawn into container 212 as needed during operation.

In some embodiments, a gas input is provided to channel 203. Potentially, a liquid:gas mixture is provided in a ratio of, for example, 10:1, 4:1, 2:1, 1:1, 1:2, any ratio in between, or another higher or lower ratio. It is a potential advantage to mix gas and fluid for more effectively breaking apart clumps of tissue. Applicant's experiments have shown that such a gas/liquid mixture can be effective in dislodging and/or breaking up clumped fecal material.

Other Status Determinations and Responses

The foregoing examples illustrate how a controller can make a status determination based on the combination of data from a group of sensors, and/or from a single sensor. In the case where a group of pressure sensors is used, the existence and general location of a blockage can be determined. In the case of a single flow sensor, the existence of a blockage can be determined. Command signals are issued by controller 213 according to the determined status.

In some embodiments of the invention, the determination of a status leads to one of several, optionally graded response from the controller 213. The response depends on the particulars of the sensed data and/or the history of the sensed data.

In some embodiments, the corrective action taken by the controller varies depending on the determination of the blockage location. Optionally, a distal-tip blockage removal routine includes momentarily stopping evacuation. Simultaneous with the change in evacuation pressure, a flushing jet is delivered through the irrigation port, potentially knocking the blockage away from the tip. A potential advantage of this is more rapid cleaning, since already evacuated particles do not have to be regurgitated and evacuated a second time. A sufficiently interior blockage, however, is not affected by a flushing jet at the distal tip. Immediately making a reversal of flow direction in the evacuation channel is potentially preferred in such a case.

In some embodiments of the invention, sensor readings are used to make a determination of the severity of the blockage. For example, a partial blockage within the evacuation channel 203 may produce readings which are intermediate between those of readings 253 and 252. In some embodiments, determination of an intermediate level of blockage is a potential determined status of the system. Optionally, the controller determines whether or not to begin a purging operation based on a threshold of blockage severity. In some embodiments, the threshold is user selectable, allowing a balance between speed of evacuation and sensitivity to potential blockage. A potential advantage of an adjustable threshold is the ability to adjust to different conditions of the bowel. For example, the evacuation phase of an evacuation/purge duty cycle may be set as long as possible for the condition of a given patient's colon without risking an unrecoverable blockage.

Another status determinable in some embodiments of the invention is the rate at which a blockage is developing. The determination by the controller to act or not on a partial blockage is optionally affected by the rate of increasing blockage. For example, a rapidly developing pressure change may be an indication of a developing hard blockage. Optionally, an incipient hard blockage is purged immediately even if the actual loss of flow is still low. In contrast, a slowly developing pressure change is optionally permitted to rise to a higher level of blockage. It may be, for example, associated with normal motions of the evacuation tube during insertion, or potentially determined to be most likely loose or self-correcting. Optionally, it is rapid fluctuations which have a lowered sensitivity, for example to filter out measurement noise and transients. Optionally, there are multiple categories of status determinable by controller 213. In some embodiments, controller 213 ignores, for example, very fast small changes, acts quickly for somewhat slower or larger changes, and sets a high threshold for response to slow changes.

The use of pressure sensors in some embodiments of the invention allows determination of system status parameters optionally including—as the above examples describe— blockages and developing blockages, including their locations, severity, and/or rate of development. Use of a pressure sensor is typical for performing these and related sensing functions in some embodiments of the current invention. In some embodiments of the invention, other types of sensors and/or sensor systems are present on, near, or in the evacuation channel or the tip of the evacuation channel. These additional inputs are optionally comprised in further forms of status determination, and potentially affect system operation.

In some embodiments of the invention, the insertion tube comprises a sensor suitable for sensing the presence of fluid. A fluid sensor is, for example: a pH sensor, an osmotic pressure sensor, and/or an electrical conductance sensor. In some embodiments, the fluid sensor is disposed on the insertion tube of the colon cleaning system to detect fluid around the distal tip of the insertion tube. Optionally, this status determination automatically initiates a fluid evacuation routine to clear the fluid, with or without a simultaneous supply of irrigating fluid.

In some embodiments, an optical sensor senses material flow by means of optical flow near the sensor. According to the embodiment, an appropriate illumination source for the sensor is provided.

In some embodiments, the optical sensor reports spectral information, allowing determination of information about the composition of the waste material. For example, the presence of blood in the waste material is potentially indicated by waste material having the spectral characteristics of hemoglobin. A potential advantage of detecting blood in waste material is the detection of hemorrhaging, which is a possibly serious complication of a colonoscopy examination. Optional actions commanded by the controller in the case of a determined unexpected hemorrhage are cessation of vacuum to the colon, and/or raising an audible or visual alert.

In some embodiments of the invention, an optical sensor indicates to the controller the amount of waste content in evacuated fluid. Waste content is measured by, for example: optical density reflecting turbidity and/or solutes, particle counts, and/or particle size. In some embodiments of the invention, there is a threshold of indicated waste content below which fluid is considered clean. Optionally, an irrigating and evacuation routine is terminated when a threshold condition (for example, of cleanliness) is met, and/or when a threshold condition is met for a preset time period. Optionally, an irrigating and/or evacuation routine starts when a view through the colonoscope is determined to be obscured.

In some embodiments, the density, turbidity, and/or conductance of the fluid being pumped indicate the presence of foaming. Potentially, sensed indications of a need for purging, and optionally the parameters of purging itself are different when handling foamed compared to unfoamed evacuation material. For example, pressure changes indicative of a forming blockage are potentially different, due to the more compressible properties of a foam compared to a liquid. Also for example, the purging of a forming blockage in the presence of foamed material in some embodiments includes a lengthened purge cycle. Optionally, the lengthened cycle is long enough so that unfoamed material can be sent distally for more energetic purging action.

In some embodiments of the invention, a record of waste content amounts evacuated during a procedure is stored and made available online and/or for later retrieval. Optionally, retrieved data is in the form of a report. Optionally, reported waste content is as a function of time and/or position in the bowel. Optionally, waste content is reported as an integrated value. Using a reliable colon cleaning system during a colonoscopy, there is a potential to modify (for example, make less aggressive) protocols for cleaning a patient's bowel before examination. In some embodiments, cleaning can be done without one or more typical bowel cleaning steps, for example fasting or directed consumption of liquids. In some embodiments, operation is prepless—performed without advance colon cleaning steps. Feedback on the effectiveness of a particular pre-exam cleaning procedure is potentially beneficial for evaluating the effectiveness of alternative protocols. Additionally and/or alternatively, an objective indication during a procedure of unacceptably high waste content in a patient colon can be used to justify a corrective action and/or aborting the procedure.

In some embodiments of the invention, sensors and or determinations which indicate a status away from the evacuation channel are available to the controller 213.

In some embodiments, sensing data and/or status indications are provided to the colon cleaning system from other systems or subsystems; for example: a colonoscope, or a clinical monitoring device. Optionally, these data and/or status indications directly trigger and/or halt a cleaning routine, or provide additional input to the controller 213 used in making operating determinations. Data and indications are communicated, for example, by a wire, optical coupling, radio, and/or another standard or specially provided communication method between the colon cleaning system and another system.

In some embodiments of the invention, for example, an automatically determined indication of the presence of obscuring material in the colonoscope view is optionally provided to controller 213. Optionally, a cleaning routine is initiated upon receipt of such an indication.

Exemplary Cleaning Routine

Figure 6:
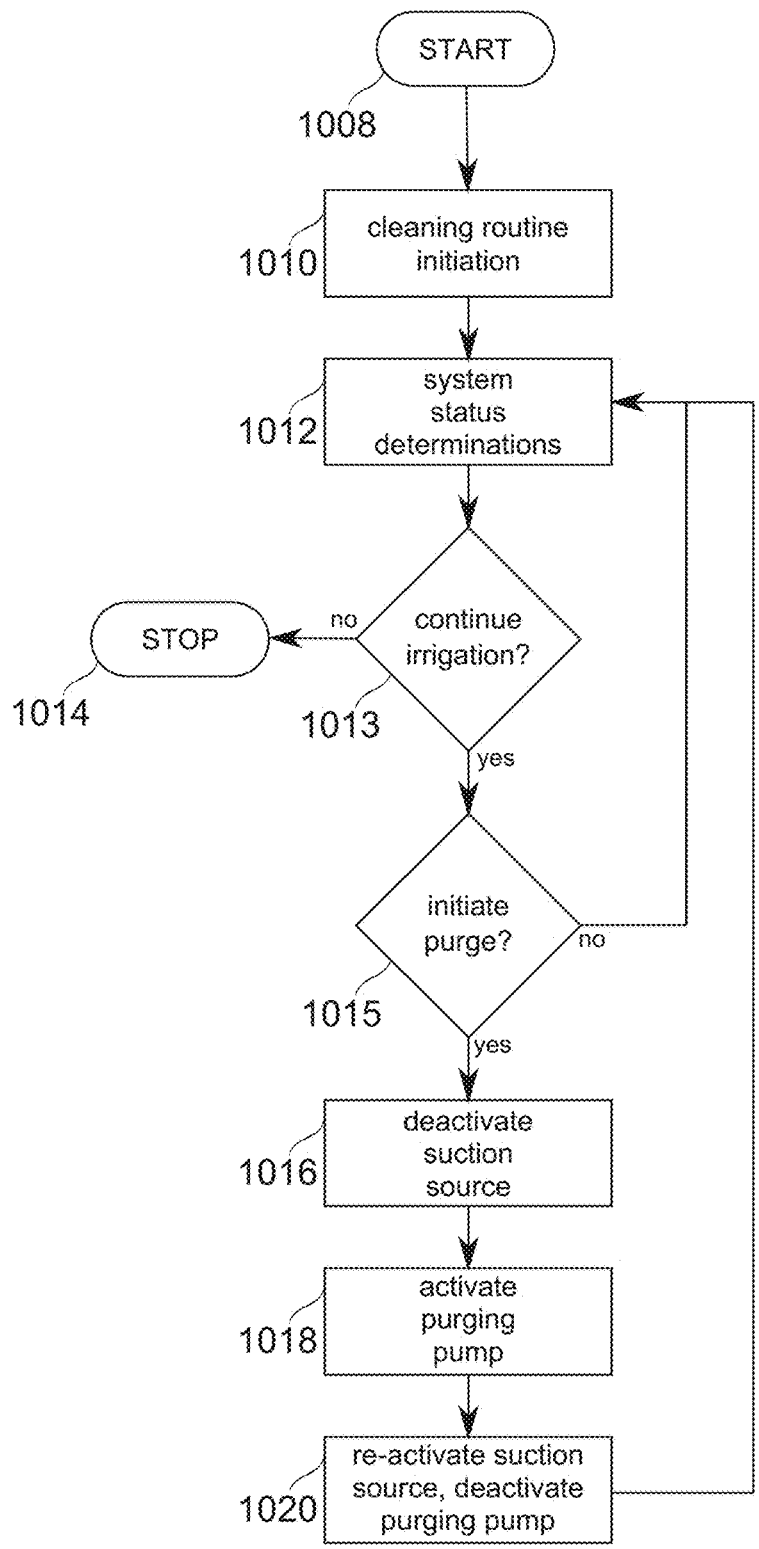
FIG. 6 is a simplified flow chart of a colon cleaning method; according to some embodiments of the present invention.

Reference is now made to FIG. 6, which is a simplified flow chart of an exemplary method for cleaning a colon, including detection and purging of blockages, according to some exemplary embodiments of the invention. The method occurs, for example, in the course of an ongoing colonoscopy exam. Reference numbers not in FIG. 6 refer to earlier figures, for example FIGS. 4A-4F. In this exemplary method, pump 214.4 is treated as a vacuum source (moving material proximally), while pump 214.3 is treated as a pump for moving material distally in evacuation channel 203.

At block 1008, a determination to initiate a cleaning routine is made, according to some exemplary embodiments of the invention. The determination is made, for example, based on an elapsed time value, a manual command of a cleaning system operator, and/or determined system status. Optionally, for example, a determination of an immersion and/or an obscured view status initiates a cleaning routine.

At block 1010, a cleaning routine initiates, according to some exemplary embodiments. Liquid is provided, for example by pump 214 through irrigation pipe 201, to irrigate a colon. Suction is provided, for example, by pump 214.4 or another vacuum source through evacuation channel 203. Suction moves fecal matter dissolved or suspended in the irrigation liquid from colon 1 proximally through channel 203. Optionally, waste is collected in waste collection device 212A. In some embodiments, the relative balance of suction and irrigation is under control by controller 213. The balance is chosen, for example, to maintain an equal volume, or alternatively to provide net suction to clear an overpressure or fluid build-up. Optionally, the control is adjusted based on monitored sensor data.

At block 1012, one or more system status determinations are made, according to some embodiments. Sensors and sensing modules, for example as described in relation to FIGS. 2A-4F or elsewhere herein, report pressure data and/or flow data to a controller 213. The controller 213 makes one or more status determinations based on reported data. It should be noted that controller 213 is optionally implemented in a distributed fashion. For example, some sensing, status determination, and control may be integral to a pump (such sensing for a shutdown in a fault condition). Other status determination and control is optionally concentrated at a CPU, FPGA, or other logic circuit of the colon cleaning system.

At block 1013, an irrigation continuation determination occurs, according to some embodiments. Controller 213 determines, for example, whether pressure safety limits are kept, whether a manual irrigation stop command has been issued, and/or whether a preset irrigation time has elapsed. If there is a determination to stop irrigation, irrigation terminates at block 1014 until next initiated.

At block 1014, irrigation terminates, according to some embodiments.

At block 1015, a purge initiation determination occurs, according to some embodiments. Controller 213 determines, for example, whether flow and/or pressure status is within parameters suitable for continuation of the cleaning process. A suitable pressure for initiation of a purge is, for example, a pressure which is determined to be within safe pressure limits for an intracolonic pressure. The safe pressure condition is, for example, a pressure less than 90-110 mmHg, less than 100-150 mmHg, less than 140-160 mmHg, or less than 150-200 mmHg. Additionally and/or alternatively, controller 213 determines if elapsed time of irrigation remains within a preset time period for irrigation before purging, and/or if no manual purging command has been issued. If there is a determination to purge, a purging routine activates at 1016. Otherwise, cleaning continues at 1010.

At block 1016, the controller 213 commands the suction pumping source 214.4 to deactivate, according to some embodiments. Optionally, irrigation pump 214 is deactivated.

At block 1018, the controller 213 commands the purging pump 214.3 to activate, according to some embodiments. Purging pump 214.3 sends water or another liquid from source 211 distally into channel 203. Potentially, this dislodges the blockage. In some embodiments, purging continues until the determination of a blockage is cancelled, and/or until a preset time has elapsed. The preset time may be, for example, 50 msec, 100 msec, 200 msec, 500 msec, 1000 msec, any time in between, or a larger or smaller time. In some embodiments, a determination of a potentially dangerous pressure level in the colon stops the purging routine (deactivating purging pump 214.3, for example). In some embodiments, the duration of the purging routine is determined by input from the operator of the device. In some embodiments, purging comprises a sequence of detailed purging actions and/or phases, as described hereinbelow.

At block 1020, the suction pumping source 214.4 is reactivated, and the purging pump 214.3 is stopped. Cleaning continues at 1012.

Details of the above method are optionally altered according to the embodiment of the invention:

In some embodiments of the invention, the role of pump 214.4 as a suction source is played, for example, by a regulated constant suction source. Such a source is, for example, a fixture in a hospital room connected to a central vacuum source, regulated through a valve. In some embodiments, pump 214.4 may thus alternatively be considered as valve 214.4. Optionally, valve 214.4 is variable (for example, under control of controller 213) to regulate the amount of suction to an amount appropriate to the determined status of the system.

In some embodiments, pump 214.4 is a bi-directional pump, driving proximal flow of matter in channel 203 during evacuating operation and driving distal flow of matter during purging operations. Purging pump 214.3 is optionally absent.

It is further noted that some individual features are shown, described, and explained with reference to specific exemplary embodiments and figures. However, it is to be understood that some embodiments of system 207 comprise combinations of features presented individually.

For example, figures presented herein illustrate sensors and sensing modules at various positions within embodiments of system 207, and operating in various ways. Other figures herein present devices and methods by which an embodiment of system 207 undertakes one of various purging operations in response sensor data and user commands. Combinations of described sensors, status determinations, and actions taken in response, are considered embodiments of the invention.

Irrigating and Evacuation Tip

Figure 7A:
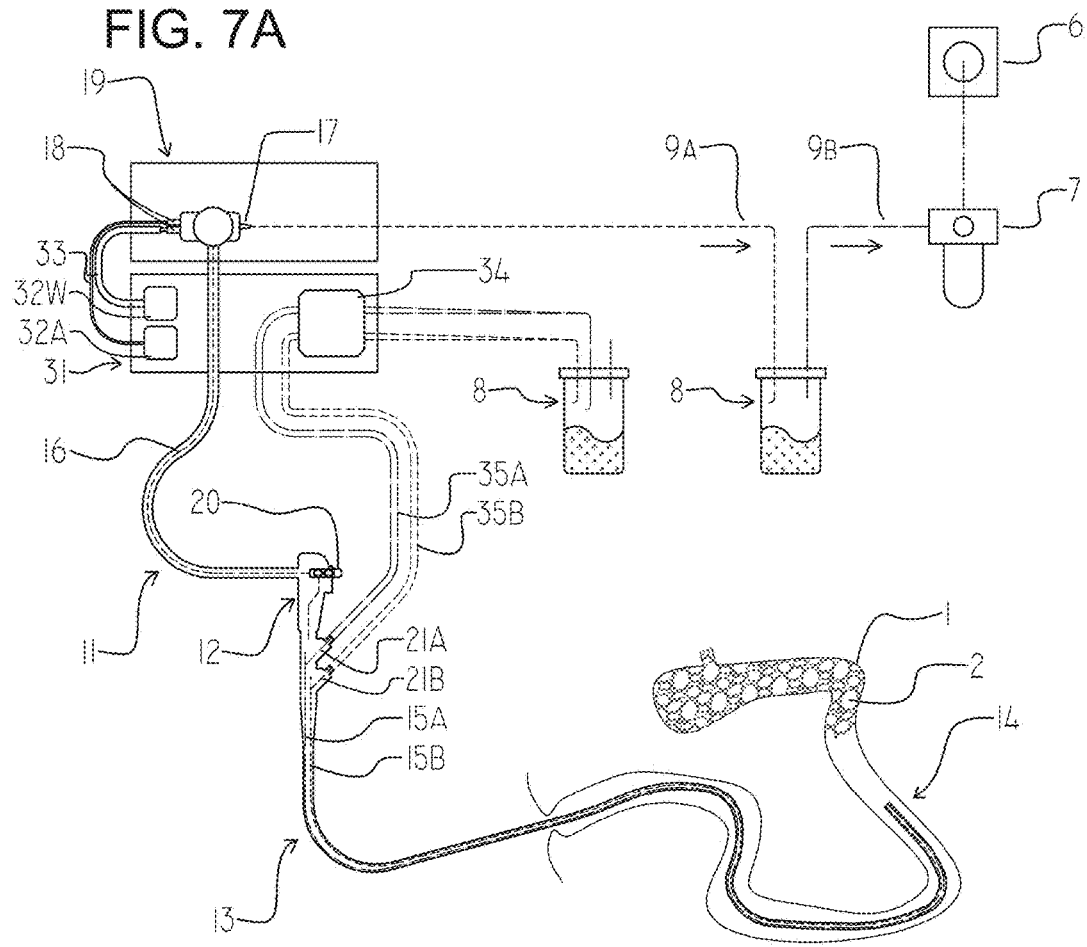
FIG. 7A schematically illustrates an exemplary colon cleaning system comprising a colonoscope workstation and a cleansing workstation, according to some embodiments of the present invention.
Figure 7B:
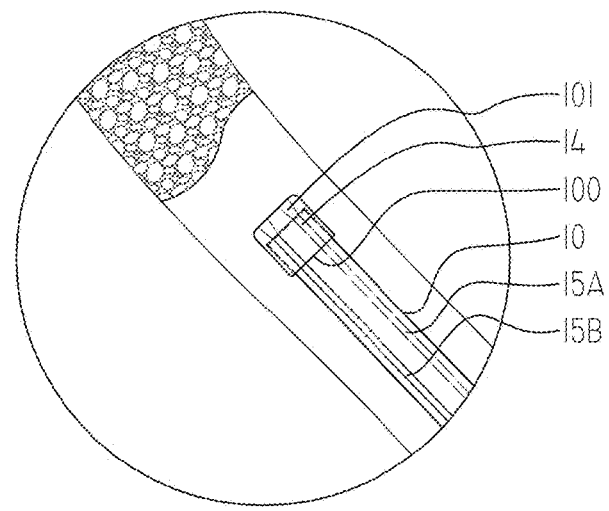
FIG. 7B schematically illustrates a magnified view of a colonoscope tip in proximity to colon content, according to some embodiments of the present invention.

Reference is now made to FIG. 7B, which schematically illustrates a tip 14 for use at the distal end of an insertion tube 13 of a colon cleansing system, according to some exemplary embodiments of the invention.

In some embodiments of the invention, tip 14 comprises an add-on adaptor element 100 at the distal end of the insertion tube of a colonoscope 10. In some embodiments, adaptor element 100 comprises plurality of intake channels fed by intake apertures 101 in fluid communication with a corresponding plurality of colonoscope working channels 15A, 15B. In some embodiments, intake channel apertures 101 comprise a distally widening shape which tapers to the dimensions of working channels 15A, 15B at their mating point. A potential advantage of adaptor element 100 is to distribute suction exerted through channels 15A, 15B over a wider distal surface area. Potentially, fluid more easily enters the widened ends of channel intake apertures 101. In some embodiments of the invention, tip 14 comprises a manifold, dividing an irrigation channel into 2, 3 4 or more outlets. Optionally, the outlets shape irrigation fluid into jets of fluid for more effective cleaning of material from the colon wall. In some embodiments, tip 14 comprises a pressure sensor for sampling pressure near the tip of the cleaning system and/or colonoscope.

Note in particular that the design of adaptor element 100 introduces the use of two or more channels for functions of a colon cleaning device. Additional details and potential advantages of a plurality of irrigating and/or flushing channels are provided hereinbelow.

Colonoscope Cleaning Systems with Multiple Channels

Reference is now made to FIG. 7A, which schematically illustrates a cleansing working station 31 wherein a plurality of irrigation and/or evacuation channels are provided, according to some exemplary embodiments of the invention.

In some embodiments, work station outlet pump 32 comprises pump 32A for supplying gas and pump 32W for supplying water.

In some embodiments of the invention, gas and water supply pumps 32A, 32W are operated simultaneously. In some embodiments, gas and water supplied under pressure are mixed (for example, in colonoscope workstation 19 or colonoscope workstation 31) to be delivered through insertion tube 13. In some embodiments, gas and water are mixed upon exiting their respective irrigation channels at tip 14. Optionally, gas and water supply pumps 32A, 32W operate separately and/or alternately. The gas supplied by pump 32A is, for example, air or carbon dioxide.

A potential advantage of supplying mixed gas and water for irrigation is to increase speed, thoroughness, and/or particle fragmentation during cleaning of colon 1. Potentially, fecal material is loosened and/or broken apart by the time-varying forces exerted by vortices of alternating gas and water created within the mixed-phase irrigation material. Potentially, gas driven into crevices of fecal matter under compressive pressure expands when pressure releases, contributing to breakup of clumped fecal matter.

In some embodiments, evacuation pump 34 comprises a plurality of inlets for a plurality of evacuation pipes 35A, 35B. In some embodiments, colonoscope handle 12 comprises a plurality of work channel inlets 21A, 21B connected to the channels of evacuation pipes 35A, 35B. In some embodiments, the work channel inlets 21A, 21B themselves connect to a plurality of independent or largely independent working channels 15A, 15B. In some embodiments, working channels 15A, 15B are working channels of a colonoscope. In some embodiments, the plurality of evacuation channels is independently operable. In some embodiments, channel operation includes reversibility, for example to purge a blockage.

A potential advantage of a plurality of evacuation channels is the increase of lumenal cross-section through which evacuation occurs. Increased lumenal cross-section potentially increases the effectiveness of evacuation, for example, the rate of evacuation. Potentially, a single unblocked channel provides sufficient evacuation capacity, and the second channel is optionally reserved as a spare. Optionally, both channels are used together, but evacuation capacity remains even after the possible loss of one due to blockage during a procedure. Optionally, one channel is used to continue evacuation of waste while operations to purge a blockage in a second channel are carried out, for example, by reversing flow direction.

Another potential advantage of a plurality of evacuation channels is reduction of the maximum diameter of the tube 13 inserted into the colon, relative to its evacuation efficacy. For example, a single evacuation channel with a diameter of 5 mm potentially adds at least 5 mm to the maximum diameter of insertion tube 13. The same cross-sectional area can be provided by, for example, two tubes of 3.5 mm diameter each, adding correspondingly less to the maximum cross-sectional of the insertion tube.

It should be noted that a non-circular shape is also possible. Potentially, however, a non-circular shape carries an increased risk of blockage for the same cross-sectional area. For example, the minimum dimension of a channel affects the maximum size of the smallest dimension of a particle which can pass through it. Also for example, a non-circular channel potentially increases regions of slow flow, which are in turn more vulnerable to blockages as a result.

According to the embodiment, the inner diameter of an evacuation channel is, for example, 2.1 mm, 3 mm, 4 mm, 4.2 mm, 4.5 mm, 5 mm, 5.5 mm, 6 mm, another larger or smaller diameter, or any diameter in between. According to the embodiment, where a plurality of channels is provided, the number of evacuation channels provided is, for example, 2, 3, 4 or more channels.

A potential advantage of a lowered diameter of an insertion tube is increased flexibility of the insertion tube 13. Increased tube flexibility in turn potentially increases the probability of successfully navigating the tube through the colon to its end, so that the colonoscopy procedure can be completed successfully.

In some embodiments, channels are joined and/or merged along a portion of their length. For example, evacuation tubes 35A, 35B may be operated through a single input aperture of evacuation pump 34. Also for example, working channels 15A, 15B may be joined at a point before reaching tip 14, for example by original design, or by addition of an attachment (not shown). An optional point of joining near a proximal end of the channels may be, for example within 10 cm, 20 cm, 40 cm, 100 cm, any length in between, or a larger or smaller length of the proximal end. An optional point of joining near a distal end is within, for example, 1 cm, 2 cm, 4 cm, 10 cm, 20 cm, 40 cm, 100 cm, any length in between, or a larger or smaller length of the distal end.

A potential advantage of proximally joining evacuation tubes 35A, 35B over a portion of their length is reduced costs, for example of tubing, or of pump elements. Another potential advantage of joining or merging evacuation tubes 35A, 35B is the sharing of a larger diameter tube where practical. Optionally, this is in portions of the channel which are external to the colon during operation.

A potential advantage of distally connecting evacuation tubes 15A, 15B is the bypassing of blockages. In an example, two evacuation channels are each fed from the same two (shared) input apertures 101 of tip 14. Thereby, a blockage in the body of one evacuation channel does not necessarily result in an otherwise unblocked tip aperture being rendered useless.

Pluralities of Evacuation Channels

Figure 8A:
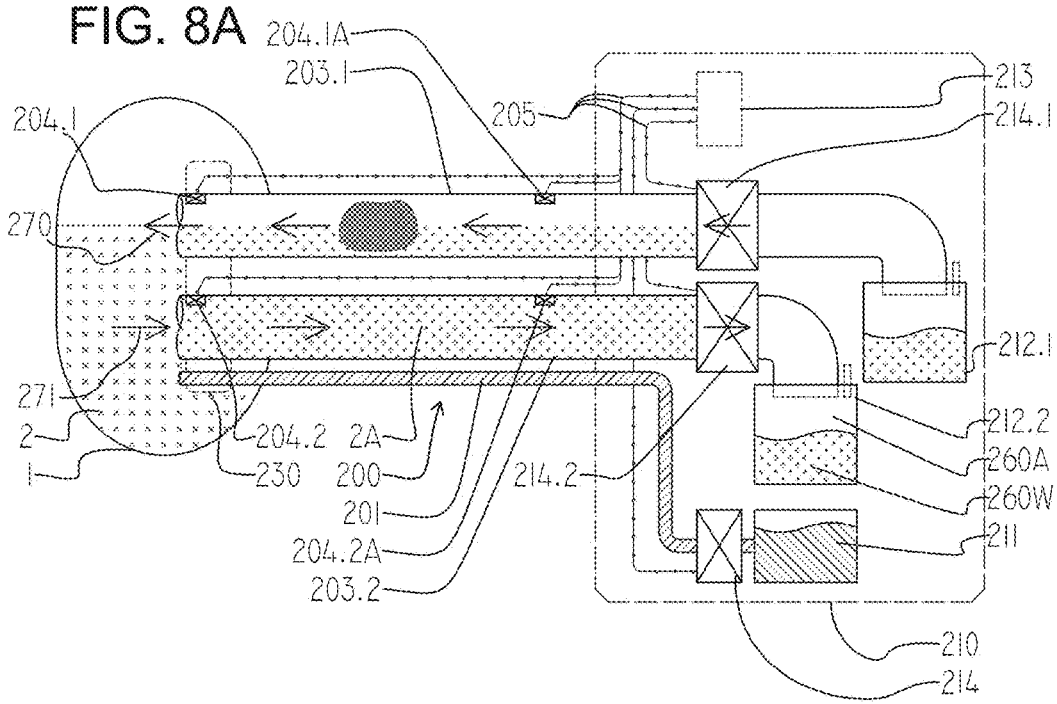
FIG. 8A schematically illustrates a cleaning system comprising two bi-directional pumps, each for a separate evacuation line, according to some embodiments of the present invention.

Reference is now made to FIG. 8A, which schematically illustrates an intestine cleaning system comprising a plurality of evacuation channels, according to some embodiments of the present invention.

In some exemplary embodiments of the invention, two evacuation channels 203.1, 203.2 interconnect the distal tip of a colon cleaning insertion tube with a proximally connected workstation. Optionally, more evacuation channels are provided.

A potential advantage of providing a plurality of evacuation channels is compactness in cross-section relative to a matched evacuation-capacity system with a single, larger-diameter evacuation channel. Another potential advantage of a plurality of evacuation channels is greater channel flexibility relative to a matched evacuation-capacity system with a single, larger evacuation channel.

It should be noted that an evacuation channel, in order to provide effective function, needs to remain open even under applied vacuum. For some embodiments of a colon cleaning device, this imposes interacting constraints which are met, according to the embodiment, by different combinations of design parameters. Particular considerations include:

The choice of tube material, where increased rigidity potentially withstands an external pressure, but potentially interferes with flexibility.

The tube lumen diameter, where lowered inner diameter potentially better withstands external pressure—particularly for a given wall thickness—but also decreases an upper size limit for fecal matter particles which can pass (there is also a potential trade-off with flexibility).

The tube lumen shape, where a circular shape, for example, provides no inherent point of collapse, but limits the opportunity to distribute cross-sectional area close to the center of the insertion tube.

The applied pressure gradient, where a higher gradient potentially allows faster evacuation through a given diameter of tubing, but increases a potential for tubing collapse, and may furthermore be limited in magnitude and/or time to avoid potential for injury.

Embodiments comprising a divided pair of circular lumens represent a functional compromise among these constraints (different from the compromise represented by a single lumen). In particular the minimum passage dimension remains large enough to pass particles of potentially blocking size, while the reduced overall diameter of the insertion tube retains flexibility and/or resists collapse. According to the embodiment, channel lumen diameter is, for example, 3 mm, 3.5 mm, 4 mm, 4.5 mm, 5 mm, 5.5 mm, 6 mm, any diameter in between, or another larger or smaller diameter.

Optionally, a more flexible material is usable with decreased lumenal cross-section. The material can be a softer silicone rubber or other material than that otherwise used in manufacture of a colonoscope or colon cleaning system insertion tube. The softness difference is a Shore A durometer decrease of, for example, 2 units, 4 units, 10 units, any value in between, or a larger or smaller unit value. Exemplary baseline Shore A durometer values for an insertion tube are between 50-70 Shore A durometer units. In some embodiments, a Shore A durometer of 40-50, or from 70-80 is used. It should be noted that pressurized fluid supplied to an insertion tube by a colon cleaning system potentially allows limited control of tube flexibility. Potentially, an inherently softer tube (when unpressurized) can nevertheless be stiffened by pressure as necessary during tube insertion.

In some embodiments, each evacuation channel 203.1, 203.2 connects to a bi-directional pump 214.1, 214.2 which both provides suction for moving material proximally in channel 203.1 or 203.2 and pumping action for moving material distally in the channels, as shown in FIG. 8A.

This specific configuration is exemplary and not limiting. For example, in some embodiments, a plurality of channels 203.1, 203.2 attaches to common vacuum sources, purge pumps 214.3, and/or bi-directional pumps 214.1, 214.2. In some embodiments, each channel 203.1, 203.2 individually connects both to an evacuation pump 214.4 (or to a connector for connecting to vacuum source outside the system) and also to a purge pump 214.3.

According to the embodiment, one or a plurality of irrigation pipes may be present. Where a plurality of irrigation pipes are provided, the pipes may be controlled individually or in combination. In the figure, irrigation pipe 201 operates to deliver irrigating fluids to a colon or other intestine portion near a distal end of evacuation channels 203.1, 203.2. Optionally, a bridging pipe (FIG. 8F illustrates an example) connects between evacuation channels 203.1, 203.2, enabling fluid to cross between channels.

Some embodiments comprising a plurality of evacuation channels 203.1, 203.2 are constructed, changed as necessary, as described herein with reference to embodiments comprising a single evacuation channel 203. Methods and features described herein as embodiments of the present invention may also be implemented, changed as necessary, using a plurality of evacuation channels 203.1, 203.2. Optionally, channels operate individually (for example, with individually controlled pumps and/or individually controlled irrigation). Optionally, channels operate in tandem (for example, with pumping and irrigation from a common source and/or from individual sources controlled to behave similarly).

In some embodiments, evacuation channels 203.1, 203.2 alternate between a first operating mode for evacuating irrigation and/or waste material proximally through a channel, and a second operating mode in which material is purged (pushed distally). Optionally, direction of flow is separately controlled for each channel 203.1, 203.2 according to any of the methods for doing so described herein.

In some embodiments, controller 213 coordinates operating modes in two or more channels. For example, a system may be controlled so that when a first channel 203.1 is in a purge mode, a second channel 203.2 is in an evacuation mode. A potential advantage of operating channels simultaneously with inverted polarity is purging of blockage in one channel while continuing to move materials out of the intestine using another channel. Another potential advantage is reduced accumulation of material in the intestine during purging in a first channel, while a nearby second channel, in evacuation mode, simultaneously evacuates purging material. It is a potential advantage for positioning and/or collapse resistance to exert positive pressure in one channel for stiffening, while continuing to evacuate material reaching the colon interior. Another potential advantage is to alternately partially stiffen channels on different sides of an insertion tube, which potentially allows limited control over distal tip position within the colon.

In embodiments providing a distal fluid bridge between evacuation channels, operating a plurality of evacuation channels in opposite directions potentially prevents purged materials from reaching the intestine. For example, materials moved distally through a first channel 203.1 potentially cross the fluid bridge to be evacuated proximally by a second channel 203.2 supplied with suction.

Operation of a Plurality of Evacuation Channels

Reference is now made to FIGS. 8B-8E, which are exemplary plots 282 (long-dashed), 283 (short-dashed) of relative pressures (Y-axis 280) versus time (X-axis 281) in a pair of evacuation channels 203.2, 203.1 (respectively), according to some exemplary embodiments of the invention.

Pressures may be considered to be measured, for example, at the location of pressure sensors 204.1A, 204.2A inside evacuation channels 203.1 and 203.2, respectively.

Figure 8B:
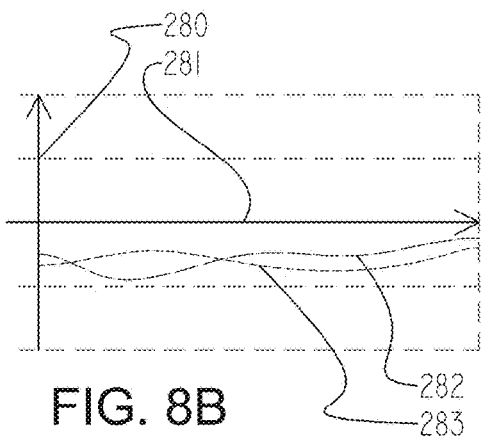
FIGS. 8B-8E are exemplary plots of relative pressure versus time in a pair of colon cleaning system evacuation channels, according to some embodiments of the present invention.

FIG. 8B represents pressure readings under conditions of unblocked, ongoing evacuation. Pressure readings are negative, reflecting suction on the channels. Readings undergo relatively small fluctuations. Fluctuations are due to, for example, sensor noise, non-blocking particles in the system, mixtures of gas and fluid in the system, and/or movements of the insertion tube.

Figure 8C:
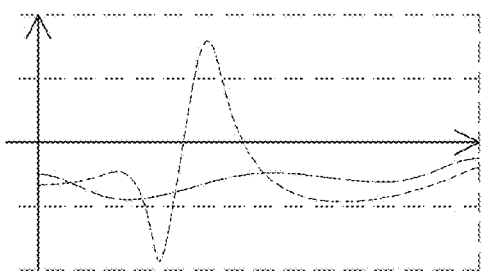

FIG. 8C represents pressure readings during a period where a blockage occurs in and is removed from a single evacuation channel 203.1 (corresponding to short-dashed plot 283). Initially, a pressure decrease is sensed at sensor 204.1A, corresponding to an increasing degree of blockage. After the minimum of this decrease, the controller 213, having determined that a blockage status exists, has sent a purging control signal to pump 214.1. The resulting reversal of pressure from pump 214.1 is reflected in the subsequent rise of pressure to a high positive value.

In some embodiments of the invention, the reversal of pressure (which is comprised in a purge operation) is initiated contingent on a determination of another condition. In some embodiments, an intracolonic pressure safety condition must be met before reversal occurs. Optionally, a pressure safety condition with two available and functioning evacuation channels purged in alternation is less stringent than the condition when only one functioning evacuation channel is operated and/or when two functioning channels present a blocked state simultaneously. A pressure safety condition for initiation of a single channel purge is, for example, a pressure less than 90-110 mmHg, less than 100-150 mmHg, less than 140-160 mmHg, or less than 150-200 mmHg. Optionally, a pressure safety condition for initiation when two functioning channels are available for use in opposite directions of flow is, for example, 5 or 10 mmHg higher (but not higher than 200 mmHg). Optionally, a pressure safety condition for initiation when two functioning channels are simultaneously purged is, for example, 10 or 20 mmHg lower.

The pressure change that is determined to correspond to a blockage is, for example, 10 mbar, 20 mbar, 30 mbar, 40 mbar, 100 mbar, any pressure in between, or a larger or smaller pressure. Optionally, a minimum time is taken to determine that a pressure change corresponds to a blockage. This is, for example, 10 msec, 20 msec, 40 msec, 100 msec, 150 msec, 200 msec, 400 msec, any time in between, or a larger or smaller time. In some embodiments of the invention, the determination of a blockage is a combined function of time and pressure, for example, a change in pressure of 10-20 mbar over 10-20 msec, 20-50 msec, 50-100 msec, or 80-200 msec; a change in 20-50 mbar over 10-20 msec, 20-50 msec, 50-100 msec, or 80-200 msec; or a change in pressure of 80-120 mbar over 20-50 msec, 50-100 msec, or 100-200 msec. In some embodiments, the change is measured as a relative change between two sensor readings, for example a relative change of 10-20 mbar, 15-40 mbar, 30-80 mbar, or 75-100 mbar.

In some embodiments, the determination of a blockage status is according to a detected flow, a detected optically sensed condition, or according to another sensed condition as described herein.

According to the embodiment, the pressure increase of FIG. 8C (represented by the plot peak) is maintained for a fixed maximum time. The time is, for example, 5 msec, 10 msec, 20 msec, 50 msec, 100 msec, 200 msec, any time in between, or a larger or smaller time. Optionally, the pressure peak is stopped when and/or maintained until a pressure change is sensed (for example, at sensor 204.1), which is determined to correspond to a freeing of the blockage. Upon a determination to continue evacuation, controller 213 sends an evacuation control signal to pump 214.1. Pump 214.1 reverses direction, pressure drops, and evacuation resumes.

Figure 8D:
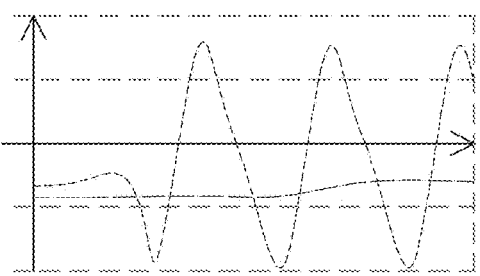

In FIG. 8D, a sequence of purging operations is shown, in which a blockage remains unresolved for at least two full purge/evacuation cycles. A purge sequence may occur, for example, if a timed purge cycle finishes, and the controller 213 determines that a blockage still exists. Alternatively, a predetermined purge routine may include a sequence of purge/evacuation cycles which are carried out without intermediate accounting for the blockage status of the system. The frequency of succeeding purge/evacuation cycles (a cycle being, for example, the period from peak evacuation pressure to purging and back to peak evacuation pressure) is, for example, 1 Hz, 2 Hz, 5 Hz, 10 Hz, 20 Hz, any frequency in between, or a larger or smaller frequency. The number of cycles in a train is, for example, 1 cycle, 2 cycles, 4 cycles, 10 cycles, 20 cycles, any number of in between, or a larger or smaller number. The number of purge trains occurring in a minute is, for example, 1-5, 3-8, 5-10, 8-20, or 15-30 distinct purging operations within a minute of system operating time. In some embodiments, the duty cycle of flow direction during purging (either distal/proximal or proximal/distal) is, for example 50% in each direction, 60%/40%, 70%/30%, 80%/20%, 90%/10%, or another duty cycle, as calculated for the portion of the overall duty cycle in which pressure is exerted. In some embodiments, there is a pause in pressure exertion comprising, for example, 5%, 10% or 20% of the overall duty cycle, during which no pressure is exerted.

In some embodiments of the invention, parameters of a purge cycle are adaptive. For example, the controller optionally tries different purging parameters during operation, and adjusts the preferred set of parameters used based on sensor readings during a purge program that indicate relative success in purging. In another example, a finding (for example, by the controller) during evacuation that trains of purge cycles are being triggered in a cluster is taken as an indication of a transient, blockage-forming clot in the system that remains a floating source of re-blockage even though it is repeatedly loosened. Optionally, an adaptive purge cycle adjustment is activated in such a situation to scrub the channel with a repeated train of cycles, prolonged beyond the determination that blockage is free, potentially breaking the problematic clot up before evacuation continues. Optionally, another purge program pumps fluid distally for a longer period than usual, in an attempt to push the blockage back out of the evacuation channel altogether.

In some embodiments of the invention, a purge cycle reduces a flow restriction in the evacuation lumen which comprises a cause other than or additional to a clot. For example, a flow restriction caused by a partial collapse of an evacuation channel under vacuum is reduced by lowering the proximally-directed pressure in the lumen of the evacuation channel. In another example, a kink in an evacuation lumen may be reduced by exerting distally-directed pressure, potentially forcing the kink to reopen. In another example, a turbulence arising in the evacuation channel, for example by exceeding a threshold of flow velocity compatible with laminar flow, may be reduced by changing the magnitude and/or direction of pressure in an evacuation channel.

In some embodiments of the invention, purging comprises variations in pressure in the same direction, optionally periodic. For example, a purging operation may continuously maintain a proximally-directed pressure, while increasing and decreasing it over time. Potentially, proximally-directed variation of pressure is sufficient to dislodge a weakly attached blockage, without a complete interruption in evacuation. In some embodiments, unidirectional pressure variations optionally alternate with variations of pressure in two directions. Potentially, this increases motion at the site of blockage (for example, as clot portions repeatedly flex to absorb changing pressure), contributing to freeing the blockage.

Figure 8E:
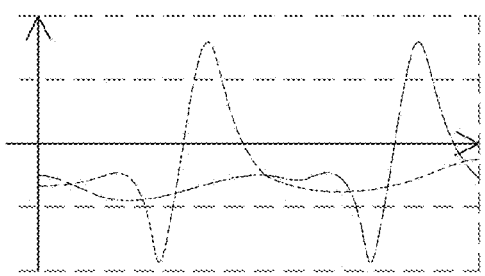
Figure 8F:
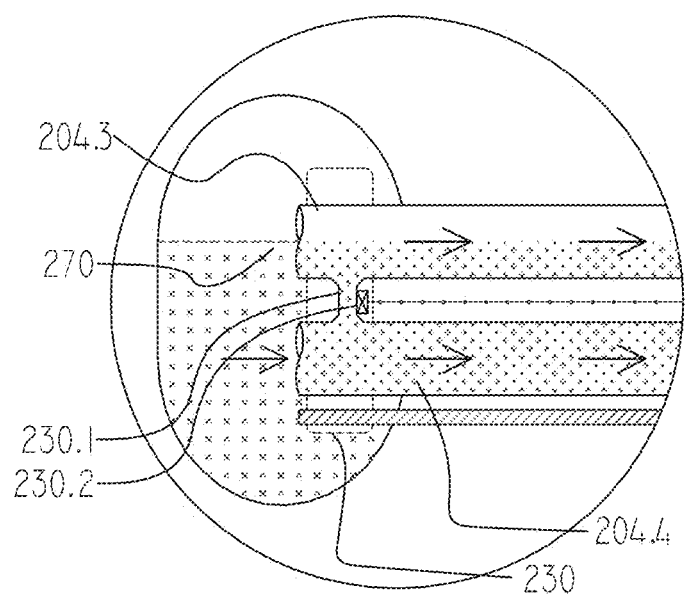
FIG. 8F is a schematic illustration of an inter-evacuation channel fluid bridge, according to some exemplary embodiments of the invention.

In FIG. 8E, an alternating sequence of purging operations is shown, in which a blockage of one channel is immediately followed by a blockage in a second channel. The phases of evacuation, blockage, purging and return to evacuation are basically as described in connection, for example, to FIG. 8C. There is an addition, in that channels operate separately. In some embodiments, purging in one channel is commanded together with increased evacuation in another, for example, to potentially maintain a net evacuation efficacy of fluid in the colon.

Reference is now made to FIG. 8F, which illustrates an inter-evacuation channel fluid bridge 230.1, according to some exemplary embodiments of the invention.

In some embodiments of the invention, a bridge 230.1 passable by fluid and/or waste is provided—for example, as part of a tip head attachment 230—which creates a connection between two evacuation channels 204.3, 204.4. In some embodiments of the invention, a sensor 230.2 such as a pressure sensor is provided to monitor conditions within the bridge 230.1.

In some embodiments, fluid bridge 230.1 plays a role in sensing if one of the intake apertures of the bridged evacuation channels 204.3, 204.4 has become at least partially blocked. In some embodiments of the invention, the pressure differential resulting from a blockage diverts a portion of the fluid entering through the intake aperture of the unblocked channel aperture to divert through the bridge to the blocked channel. This produces a sensed change, for example, a pressure drop or a flow indication, which is optionally used as an indication of a blockage formation at the distal tip. In some embodiments of the invention, bridge 230.1 allows sharing by two or more channels of a single tip aperture, potentially permitting a larger portion of evacuation capacity to be maintained if one intake aperture becomes blocked during use.

Disposable Pipe Apparatus

Figure 9A:
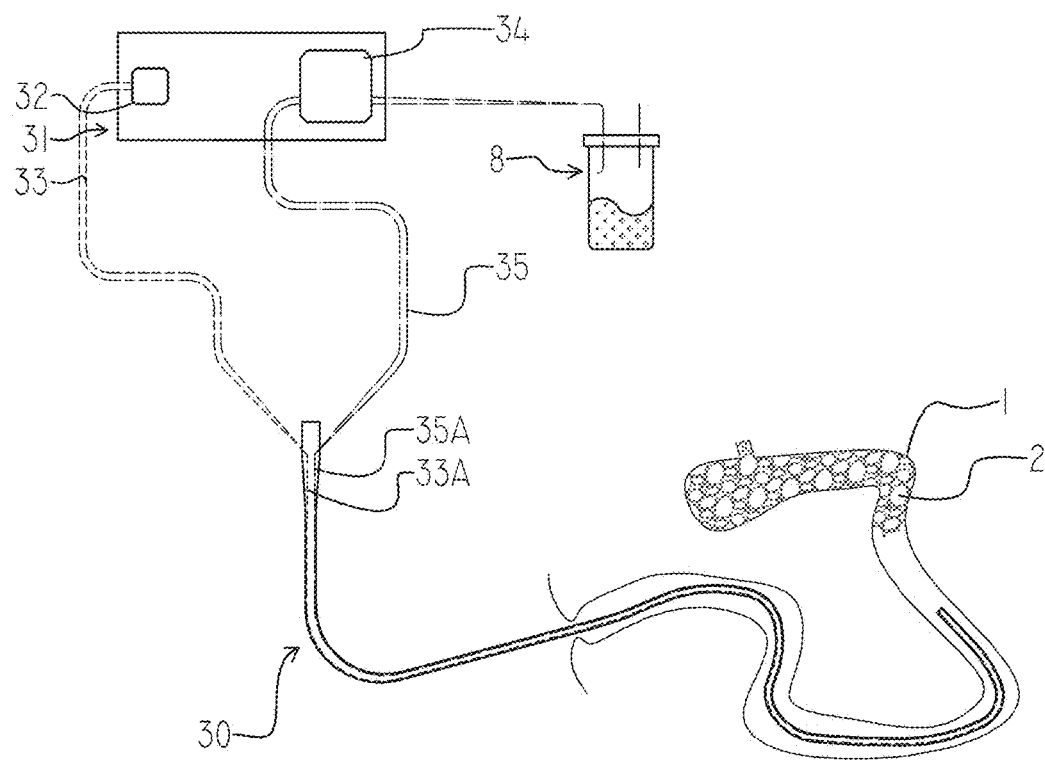
FIG. 9A schematically illustrates an exemplary cleansing working station with a disposable tube assembly comprising a water and/or air pipe for irrigation, and an evacuation pipe, according to some embodiments of the present invention.
Figure 9B:
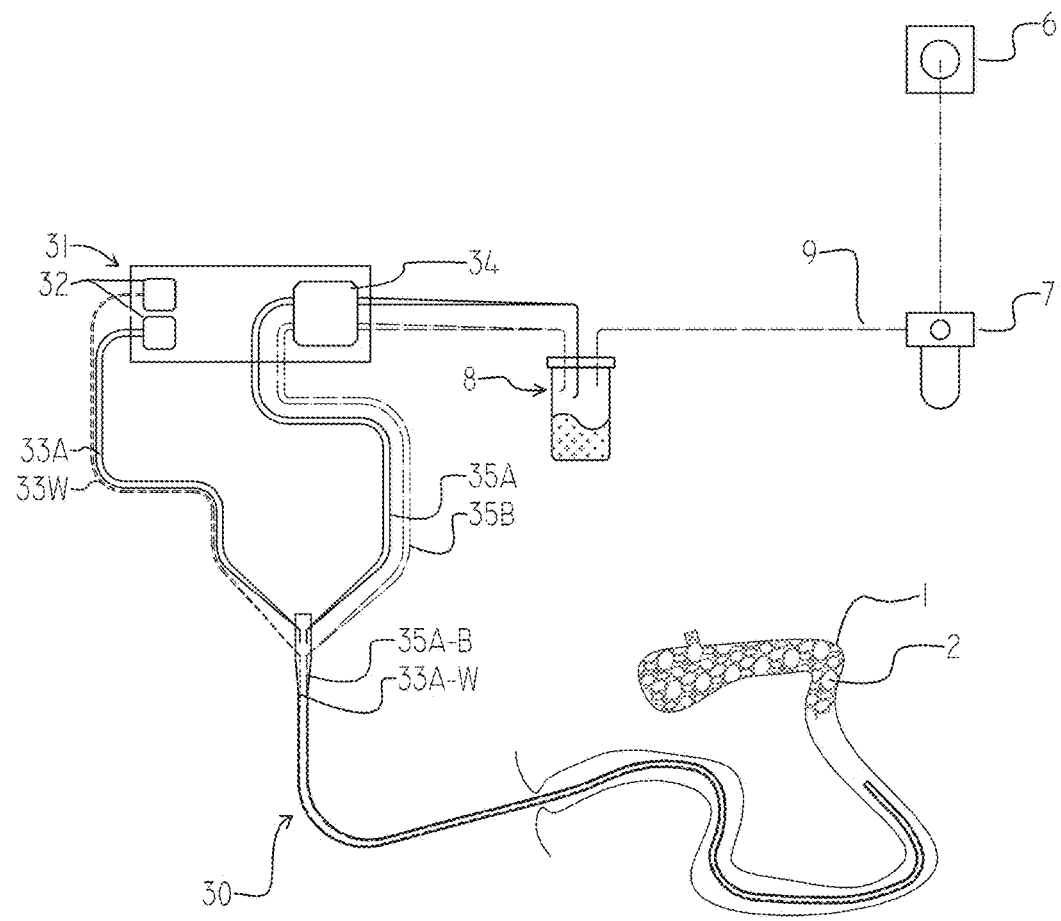
FIG. 9B schematically illustrates an exemplary cleansing working station having a disposable tube assembly comprising air and water pipes for irrigation and for dual-channel evacuation, according to some embodiments of the present invention.
Figure 10:
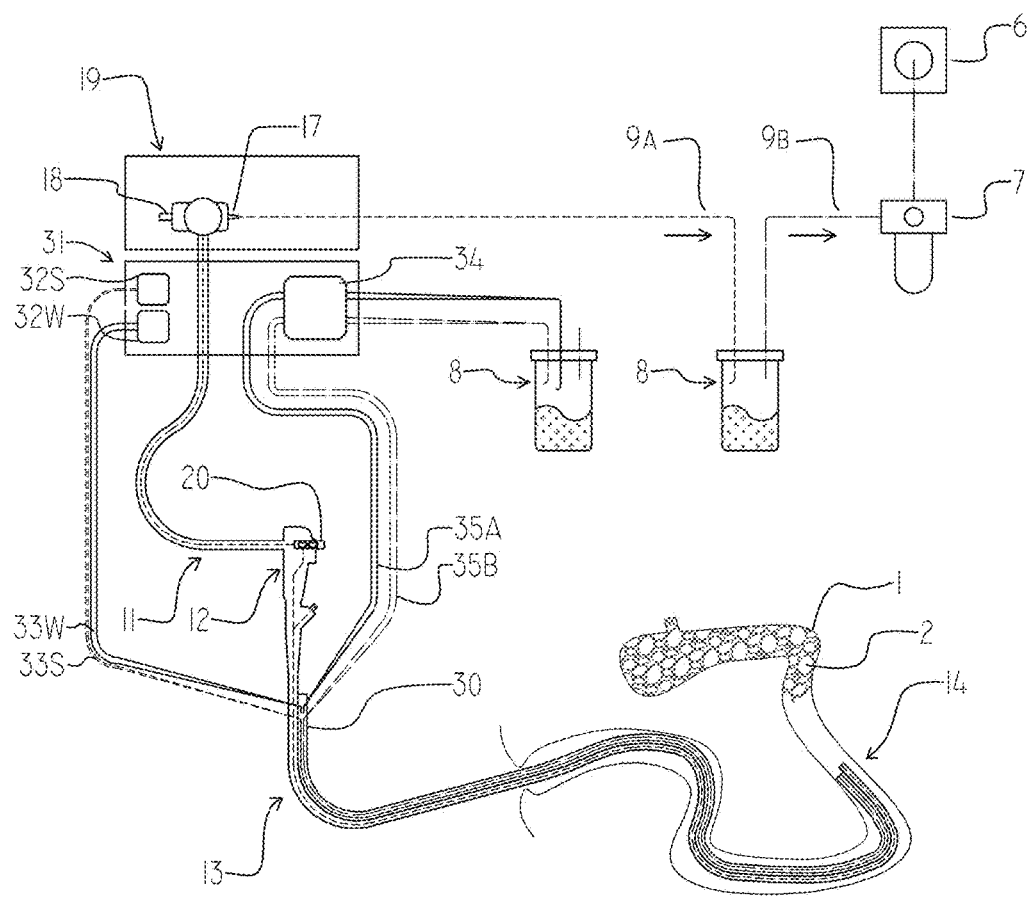
FIG. 10 schematically illustrates a colon working station together with a cleansing working station and a disposable apparatus, according to some embodiments of the present invention.

Reference is now made to FIG. 9A, which schematically illustrates a cleansing workstation 31 with a colonoscope add-on tube assembly 30 comprising irrigation pipe 33A, and evacuation pipe 35A, according to some exemplary embodiments of the invention. Reference is also made to FIG. 9B, which schematically illustrates an exemplary cleansing workstation 31 wherein disposable tube assembly 30 comprises gas and water pipes 33A, 33W for irrigation and evacuation pipes 35A, 35B. Reference is also made to FIG. 10, which schematically illustrates an exemplary colonoscope workstation 19 operating adjacent to cleansing work station 31.

In some embodiments of the invention, add-on tube assembly 30 is a tube for colon insertion. In some embodiments of the invention, tube assembly 30 is disposable. Optionally, the assembly is used for irrigation without a colonoscope.

A potential advantage of using a disposable tube assembly 30 for patient-contacting portions of a colonoscope cleaning system is to remove a need for cleaning and/or resterilization between uses. Another potential advantage of disposable tube assembly 30 is to allow rapid changeover in the event of an irreversible blockage in the disposable tube assembly 30 tubing.

In some embodiments of the invention, add-on tube assembly 30 is attachable to a colonoscope to be inserted into the colon 1 together with the colonoscope insertion tube 13. In some embodiments, disposable tube assembly 30 comprises water tube pipe 33W and gas tube pipe 33S operating together for irrigation and/or sensing. In some embodiments, evacuation pipes 35A, 35B operate together and/or separately for evacuation.

A potential advantage of an add-on tube assembly 30 is to allow use of a colon cleaning system, for example, as a retrofit, with an existing colonoscope system. Another potential advantage of an add-on tube assembly is to keep existing channels of a colonoscope, for example, working channels, continuously free for use.

In some embodiments, pumps 32S, 32W supply different irrigation materials (for example, gas and water) via tubes 33W, 33S through disposable tube assembly 30 to colonoscope tip 14. In some embodiments, pump 32S creates a pressure used in remote pressure sensing, as described, for example, with reference to FIGS. 3A-3E. In some embodiments, pump 34 provides the pressure differentials which move irrigation material into fluids container 8 via tubes 35A, 35B through disposable tube assembly 30 from colonoscope tip 14. In some embodiments, colonoscope tip 14 thereby supplies both irrigation material and irrigation material evacuation in the cleaning of fecal matter 2 from colon 1.

In some embodiments of the invention, colonoscope work station 19 independently evacuates fecal matter. In some embodiments, a pressure differential for suction is provided by vacuum wall inlet 6 through regulator 7 via pipe 9. In some embodiments, pipe 9 connects in turn through vacuum inlet 17 to colonoscope inner pipes 11, insertion tube 13, and tip 14. Through this series of connections, fecal matter 2 is collectable by tip 14 into container 8.

Cleansing System with Disposable Tube Assembly

Figure 11:
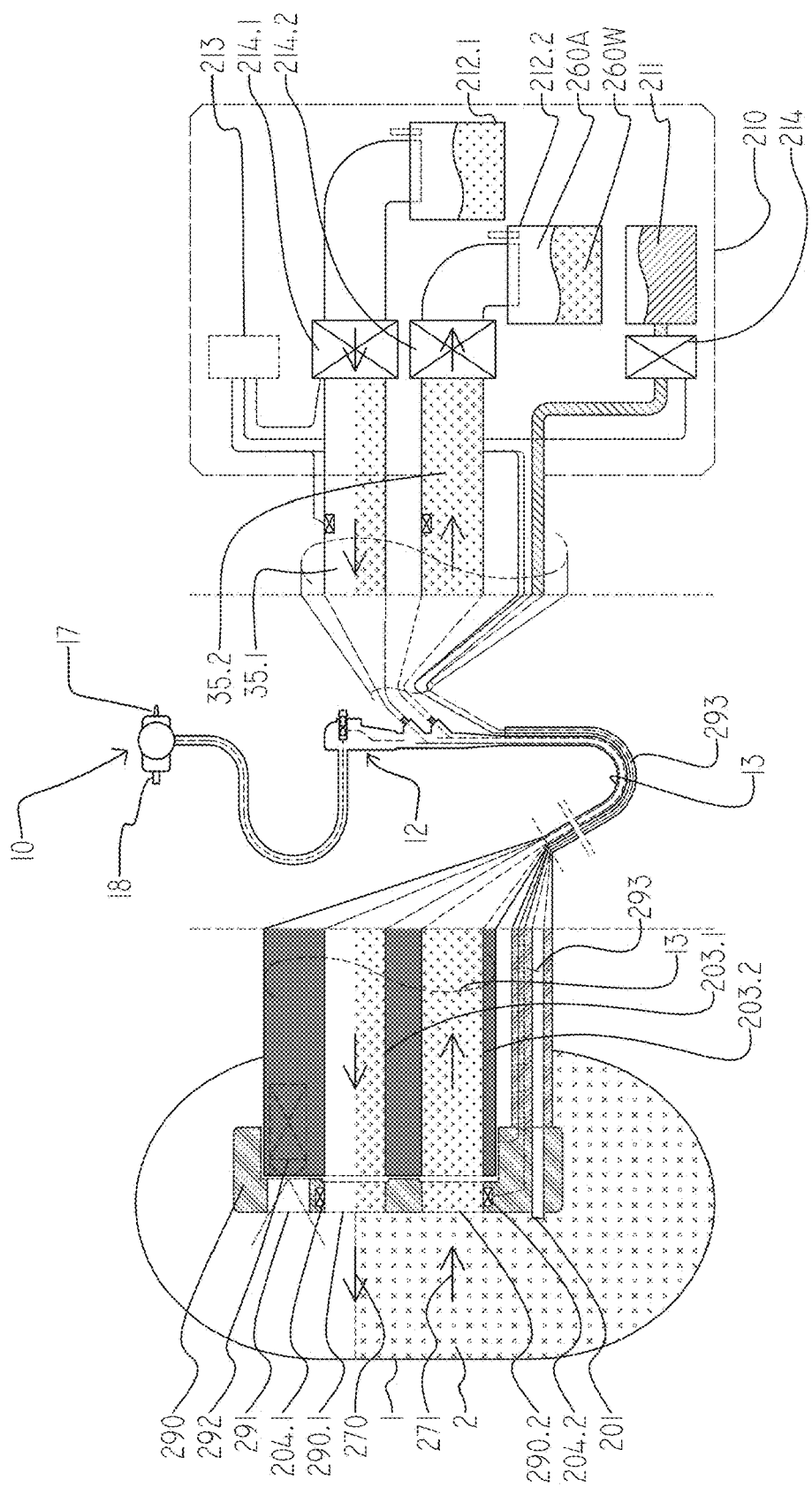
FIG. 11 schematically illustrates a cleaning system comprising two bi-directional pumps together with a colonoscope, according to some embodiments of the present invention.

Reference is now made to FIG. 11, which schematically illustrates an exemplary colon cleaning system comprising an add-on tube assembly and two bi-directional pumps together with a colonoscope, according to some exemplary embodiments of the invention.

In some embodiments of the invention, cleansing system 207 is attached to the probe of colonoscope 10. In some embodiments, evacuation tubes 35.1, 35.2 and irrigation tube 201 form disposable tube assembly 293. The disposable tube assembly 293 and the colonoscope insertion tube 13 are assembled with a common distal head housing 290 at the tip. The disposable tube assembly 293 intubates colon 1 and evacuates fecal matter 2 along with insertion tube 13. Suction 271 and evacuation 270 are controlled by work station 210 as described hereinabove.

In some embodiments of the invention, distal head housing 290 provides a framework for the mounting of sensors 204.2, 204.1, which attach to workstation 210 through tube assembly 293. In some embodiments, distal head housing 290 comprises apertures for evacuation 290.1, 290.2 which permit access to the working channels 203.1, 203.2 of insertion tube 13. In some embodiments, distal head housing 290 also provides an imaging aperture 291 for colonoscope imaging device 292 and/or associated illumination.

A potential advantage of using a head housing 290 is to allow add-on cleansing functionality together with an existing colonoscope. Some exemplary embodiments of the invention comprise a colonoscope originally designed to provide cleansing functionality as described herein, including purpose-provided irrigation and evacuation channels. In some embodiments, cleansing functionality is provided as an entirely separate tubing system, which does not interfere with the functions of a pre-existing colonoscope that it works alongside of. In some embodiments, such as that of FIG. 11, the pre-existing colonoscope functionality is at least partially co-opted into cleaning. Optionally, one or more of the colonoscope working channels are used, at least part of the time, as evacuation channels for removing irrigation material from the colon. Optionally, functions such as irrigation and the directing of irrigation fluid are provided by one or more add-on units provided by the cleaning system. In such embodiments, head housing 290 optionally plays a role in integrating the structures of the colonoscope to the structures of the cleaning system. Furthermore, in some embodiments, with some portions of the tubing potentially usable either for cleansing or as working channels, the overall probe diameter can be reduced compared to that required for supporting each function independently.

As used herein the term "about" refers to within ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A system for cleaning an intestine, comprising:
   an evacuation lumen for evacuating irrigation fluid from said intestine;
   a pressure source;
   at least one sensor, positioned to detect an environmental condition in or near said evacuation lumen; and
   a controller configured to:
   measure a flow status of said evacuation lumen based on reporting from said at least one sensor,
   determine that the flow status indicates incipient blockage before the incipient blockage amounts to more than a 40% impairment of flow, and
   adjust the pressure from said pressure source to prevent said incipient blockage from increasing, based on said determination;
   wherein said being configured to determine that the flow status indicates incipient blockage comprises being configured to determine a location in the system of the incipient blockage, said location being a basis on which the pressure is adjusted.

2. The system of claim 1, wherein said pressure source is operable to alternately apply proximally-directed and distally-directed pressure gradients to said evacuation lumen.

3. The system of claim 1, wherein said incipient blockage is determined while the rate of evacuation matches or exceeds a rate of introduction of said irrigation fluid to said intestine.

4. The system of claim 1, wherein said controller is configured to determine indication of the incipient blockage while the incipient blockage comprises less than a 50% occlusion of a cross-section of the evacuation lumen.

5. The system of claim 1, wherein said controller is configured to determine indication of the incipient blockage while the incipient blockage comprises less than a 10% occlusion of a cross-section of the evacuation lumen.

6. The system of claim 1, wherein said incipient blockage comprises a decreasing rate of evacuation due to increasing obstruction of an evacuation lumen.

7. The system of claim 1, wherein said being configured to adjust the pressure comprises being configured to adjust through at least two cycles of increasing and then decreasing a distally directed pressure.

8. The system of claim 1, wherein said controller is configured to re-measure the flow status and to redetermine indication of incipient blockage therefrom during said adjusting of pressure, and to control said adjusting of the pressure based upon finding that the indication of incipient blockage is continued.

9. The system of claim 1, wherein said at least one sensor comprises a plurality of sensors selected from a group consisting of:
   (a) a sensor positioned on external surface of a distal portion of said evacuation lumen and external to said lumen;
   (b) a sensor positioned within said evacuation lumen and within 5 mm of a distal end of said evacuation lumen;
   (c) a sensor positioned within said evacuation lumen and 5-30 mm of a distal end of said evacuation lumen;
   (d) a sensor positioned within said evacuation lumen and 3-160 cm from a distal end of said evacuation lumen;
   (e) a sensor positioned within said evacuation lumen and 160-250 cm from a distal end of said evacuation lumen;
   (f) a sensor positioned within said evacuation lumen and at least 250 cm from a distal end of said evacuation lumen; and
   (g) a sensor positioned within a fluid supply tube which supplies a fluid flow to a distal portion of said evacuation lumen.

10. The system of claim 1, wherein said being configured to measure a flow status comprises being configured to measure at least one of the group consisting of a change in a sensed:
   (a) pressure from one or more sensors;
   (b) pressure difference among two or more sensors;
   (c) flow;
   (d) optical property; and
   (e) bulk material property.

11. The system of claim 1, wherein said system comprises a plurality of evacuation lumens; and
   the pressure applied to each of said plurality of evacuation lumens by said pressure source is individually controllable.

12. The system of claim 1, wherein:
said at least one sensor is positioned to detect pressure in said evacuation lumen; and
said being configured to measure a flow status comprises being configured to measure a pressure change in said evacuation lumen.

13. The system of claim 1, comprising:
an intestinal pressure sensor positioned to sense pressure within the intestine, outside of the evacuation lumen; and
an irrigation supply channel supplying irrigation fluid to said intestine;
said controller being configured to:
determine an inflation pressure of said intestine based on reporting from said intestinal pressure sensor, and
vary the supply of irrigation fluid to said intestine based on said determination.

14. The system of claim 1, wherein said controller is configured to determine indication of the incipient blockage before the incipient blockage amounts to more than a 20% impairment of flow in the evacuation lumen.

\* \* \* \* \*